US010070997B2

(12) United States Patent
Nishikawa et al.

(10) Patent No.: US 10,070,997 B2
(45) Date of Patent: Sep. 11, 2018

(54) ABSORBENT PANT WITH ADVANTAGEOUSLY CHANNELED ABSORBENT CORE STRUCTURE AND BULGE-REDUCING FEATURES

(71) Applicant: The Procter & Gamble Company, Cincinnati, OH (US)

(72) Inventors: Masaharu Nishikawa, Cincinnati, OH (US); Gary Dean LaVon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 805 days.

(21) Appl. No.: 14/598,861

(22) Filed: Jan. 16, 2015

(65) Prior Publication Data

US 2016/0206482 A1 Jul. 21, 2016

(51) Int. Cl.
| | |
|---|---|
| *A61F 13/15* | (2006.01) |
| *A61F 13/49* | (2006.01) |
| *A61F 13/494* | (2006.01) |
| *A61F 13/496* | (2006.01) |
| *A61F 13/532* | (2006.01) |
| *A61F 13/533* | (2006.01) |
| *A61F 13/45* | (2006.01) |

(52) U.S. Cl.
CPC .. *A61F 13/49011* (2013.01); *A61F 13/49001* (2013.01); *A61F 13/496* (2013.01); *A61F 13/49017* (2013.01); *A61F 13/49406* (2013.01); *A61F 13/532* (2013.01); *A61F 13/533* (2013.01); *A61F 2013/4587* (2013.01); *A61F 2013/4948* (2013.01)

(58) Field of Classification Search
CPC .......... A61F 13/49011; A61F 13/49017; A61F 13/49406; A61F 13/496; A61F 13/532; A61F 13/533; A61F 2013/4587; A61F 2013/4948
USPC ............ 604/385.23, 385.24, 385.26, 385.27, 604/385.29, 385.3
See application file for complete search history.

(56) References Cited

U.S. PATENT DOCUMENTS

| | | | |
|---|---|---|---|
| 4,854,984 A | 8/1989 | Ball et al. | |
| 4,919,738 A | 4/1990 | Ball et al. | |
| 5,266,392 A | 11/1993 | Land et al. | |
| 5,340,648 A | 8/1994 | Rollins et al. | |
| 5,382,400 A | 1/1995 | Pike et al. | |
| 5,418,045 A | 5/1995 | Pike et al. | |
| 5,501,756 A | 3/1996 | Rollins et al. | |

(Continued)

FOREIGN PATENT DOCUMENTS

WO WO 2009-155265 A2 12/2009

OTHER PUBLICATIONS

PCT International Search Report, dated Apr. 25, 2016 (12 pages).

*Primary Examiner* — Jacqueline Stephens
(74) *Attorney, Agent, or Firm* — William E. Gallagher

(57) ABSTRACT

A disposable absorbent pant having a belt structure and a longitudinally channeled absorbent core structure is disclosed. The channels include at least one shorter, at least partially transversely-oriented secondary channel in the front and/or rear, to provide a hinge structure in the core, enabling the core to flex laterally and reduce the likelihood of undesirable bulging in the front and/or rear of the pant while it is worn, after the core has absorbed liquid and stiffened longitudinally as a result of the channeled structure.

17 Claims, 23 Drawing Sheets

(56) References Cited

U.S. PATENT DOCUMENTS

| | | | |
|---|---|---|---|
| 5,507,909 A | 4/1996 | Rollins et al. | |
| 5,622,772 A | 4/1997 | Stokes et al. | |
| 5,707,468 A | 1/1998 | Arnold et al. | |
| 6,077,375 A | 6/2000 | Kwok | |
| 6,200,635 B1 | 3/2001 | Kwok | |
| 6,235,137 B1 | 5/2001 | Van Eperen et al. | |
| 6,361,634 B1 | 3/2002 | White et al. | |
| 6,454,989 B1 | 9/2002 | Neely et al. | |
| 6,520,237 B1 | 2/2003 | Bolyard et al. | |
| 6,561,430 B2 | 5/2003 | Ou | |
| 6,582,518 B2 | 6/2003 | Riney | |
| 6,610,161 B2 | 8/2003 | Erdman | |
| 6,613,146 B2 | 9/2003 | Bolyard | |
| 6,632,386 B2 | 10/2003 | Shelley et al. | |
| 6,645,569 B2 | 11/2003 | Cramer et al. | |
| 6,652,693 B2 | 11/2003 | Burriss et al. | |
| 6,719,846 B2 | 4/2004 | Nakamura et al. | |
| 6,737,102 B1 | 5/2004 | Saidman et al. | |
| 6,863,933 B2 | 3/2005 | Cramer et al. | |
| 7,112,621 B2 | 9/2006 | Rorhbaugh et al. | |
| 7,291,239 B2 | 11/2007 | Polanco et al. | |
| 7,744,576 B2 | 6/2010 | Busam et al. | |
| 7,838,722 B2 | 11/2010 | Blessing et al. | |
| 8,017,827 B2 | 9/2011 | Hundorf et al. | |
| 8,180,603 B2 | 5/2012 | Blessing et al. | |
| 8,445,744 B2 | 5/2013 | Autran et al. | |
| 8,496,637 B2 | 7/2013 | Hundorf et al. | |
| 8,581,019 B2 | 11/2013 | Carlucci et al. | |
| 8,728,051 B2 | 5/2014 | Lu et al. | |
| 8,979,815 B2 | 3/2015 | Roe et al. | |
| 2003/0148684 A1 | 8/2003 | Cramer et al. | |
| 2005/0008839 A1 | 1/2005 | Cramer et al. | |
| 2005/0288648 A1 | 12/2005 | Otsubo et al. | |
| 2006/0030831 A1 | 2/2006 | Matsuda et al. | |
| 2007/0093767 A1 | 4/2007 | Carlucci et al. | |
| 2008/0312617 A1 | 12/2008 | Hundorf et al. | |
| 2008/0312618 A1 | 12/2008 | Hundorf et al. | |
| 2008/0312619 A1 | 12/2008 | Ashton et al. | |
| 2008/0312620 A1 | 12/2008 | Ashton et al. | |
| 2008/0312621 A1 | 12/2008 | Hundorf et al. | |
| 2008/0312622 A1 | 12/2008 | Hundorf et al. | |
| 2008/0312625 A1 | 12/2008 | Hundorf et al. | |
| 2008/0312628 A1 | 12/2008 | Hundorf et al. | |
| 2009/0318884 A1 | 12/2009 | Meyer et al. | |
| 2012/0316526 A1 | 12/2012 | Rosati et al. | |
| 2012/0316528 A1 | 12/2012 | Kreuzer et al. | |
| 2012/0316529 A1* | 12/2012 | Kreuzer | A61F 13/533 604/366 |
| 2013/0046266 A1 | 2/2013 | Kawakami | |
| 2013/0211355 A1 | 8/2013 | Nishikawa et al. | |
| 2013/0245588 A1 | 9/2013 | Mishima et al. | |
| 2013/0289509 A1 | 10/2013 | Mukai et al. | |
| 2014/0005628 A1 | 1/2014 | LaVon et al. | |
| 2014/0163501 A1 | 6/2014 | Ehrnsperger et al. | |
| 2014/0163503 A1 | 6/2014 | Arizti et al. | |
| 2014/0163511 A1 | 6/2014 | Roe et al. | |
| 2014/0276525 A1 | 9/2014 | LaVon et al. | |
| 2014/0371701 A1 | 12/2014 | Bianchi et al. | |
| 2016/0100999 A1* | 4/2016 | Hamilton | A61F 13/49011 604/372 |

* cited by examiner

ABSORBENT PANT WITH ADVANTAGEOUSLY CHANNELED ABSORBENT CORE STRUCTURE AND BULGE-REDUCING FEATURES

BACKGROUND OF THE INVENTION

In order to maintain or grow their market share, manufacturers of disposable absorbent articles such as disposable diapers and absorbent pants must continue to discover and develop improvements to materials, components and features that affect aspects such as containment, absorbency, comfort, fit and appearance. Absorbent pants are manufactured in smaller sizes to be used as, e.g., pull-on diapers and toilet training pants for young children, and in larger sizes to be used as, e.g., undergarments for persons such as adults or older children suffering from incontinence. In some applications the consumer and/or wearer may prefer that the article have an appearance and feel resembling ordinary underwear when worn.

A particular type of absorbent pant design currently marketed is sometimes called the "balloon" pant. The balloon pant design usually includes a central absorbent chassis including the absorbent core and an elastic belt. The elastic belt is usually relatively wide (in the longitudinal direction) and elastically stretchable in the lateral direction. It entirely encircles the wearer's waist, and thereby covers a relatively large amount of the wearer's skin, and also makes up a relatively large portion of the visible outside surfaces of the pant. The belt is often formed of two layers of nonwoven web sandwiching one or more elastic members such as a plurality of laterally-oriented strands or strips of elastomeric material, or a section of elastomeric film, elastomeric scrim or elastomeric nonwoven. It is common among such designs that, in manufacture, the elastic member(s) are sandwiched between the nonwoven web layers while in a strained condition.

The absorbent core structure that is part of the central chassis portion plays an important role in containment and absorbency of exudates, as well as in comfort, fit and appearance of the article when worn. In recent years, absorbent core designs have progressed toward structures with relatively higher proportions by weight of absorbent polymer particles and lower proportions of absorbent fiber (e.g., cellulose fiber), resulting in structures that are thinner than absorbent core designs of earlier years and enabling manufacture of products that are less bulky and more closely-fitting (e.g., more underwear-like) when dry. The latter structures, however, can be slower in liquid acquisition rate, and because of their greater proportions of absorbent polymer particles, can become saggy, bulky and gelatinous when wetted. To address these issues, absorbent structures including longitudinally-oriented channels have been developed. Appropriately located and structured longitudinal channels can help distribute liquid along deposits of absorbent polymer particles along the length of the absorbent core, and thereby help improve acquisition rate. They also can help reduce chances of a saggy and bulky appearance of the article when wetted, by providing longitudinal structural rigidity through the crotch region of the article resulting from pressure within the wetted absorbent polymer particle deposits between the channels.

However, it has been discovered that this structural rigidity may have undesirable effects on appearance, fit and and/or comfort. In particular, the longitudinal structural rigidity can cause the front and/or rear regions of the absorbent core to tend to bulge outwardly from the wearer's body in the front and/or rear, resulting in bulky protrusion(s) that can create an unsightly appearance and adversely impact comfort.

Thus, there continues to be room for improvements in absorbent pant design that enable realization of the benefits of various developments to date while mitigating adverse effects of these features, both when the pant is dry, and after it is wetted.

BRIEF DESCRIPTION OF THE DRAWINGS

In the drawings, the same features are numbered consistently throughout the various views and depictions of examples.

DETAILED DESCRIPTION OF THE INVENTION

As used herein "absorbent core" refers to a component of an absorbent article disposed between a topsheet and backsheet of an absorbent article. The absorbent core of an absorbent article may include one or more absorbent structures and optionally further layers, such as, for example, a cover layer.

"Absorbent polymer particles" as used herein refers to substantially water-insoluble polymer particles that can absorb at least 10 times their weight of a 0.9% saline solution in de-mineralized water as measured using the Centrifuge Retention Capacity test (EDANA 441.2-01).

As used herein "absorbent structure" refers to a three dimensional structure useful to absorb and contain liquids, such as urine. The absorbent structure may be the absorbent core of an absorbent article or may be part of the absorbent core of an absorbent article, i.e. an absorbent component of the absorbent core, as will be further described herein.

The term "basis weight" as used herein refers to the mass of a material per unit surface area it occupies when laid out on a flat surface, e.g. the mass of absorbent polymer particles deposited per unit surface area of a supporting substrate, expressed in, e.g., grams per square meter (gsm).

Figure 2A:
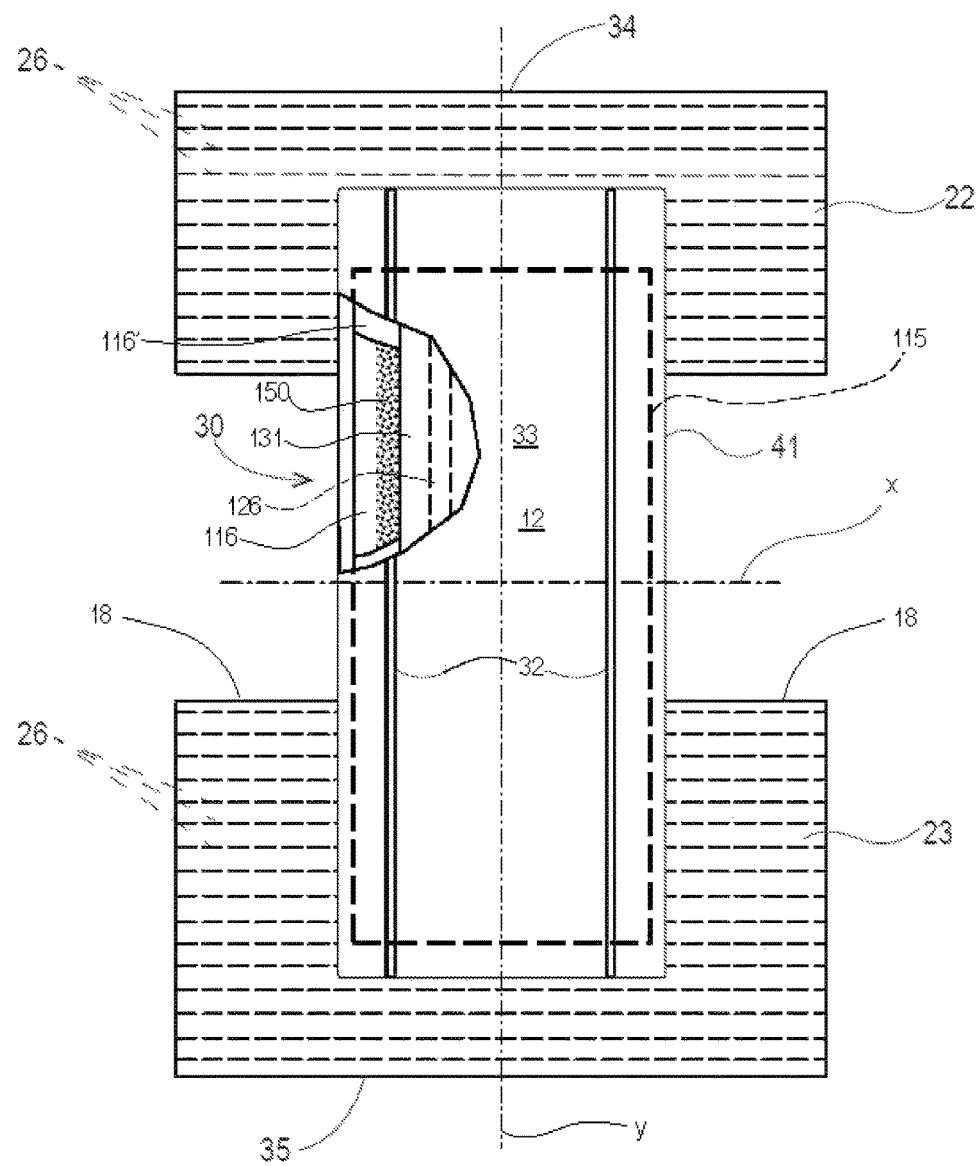
FIG. 2A is a schematic plan view of a balloon pant precursor structure, prior to joining of the front and rear belt portions at side seams, wearer-facing surfaces facing the viewer.
Figure 2B:
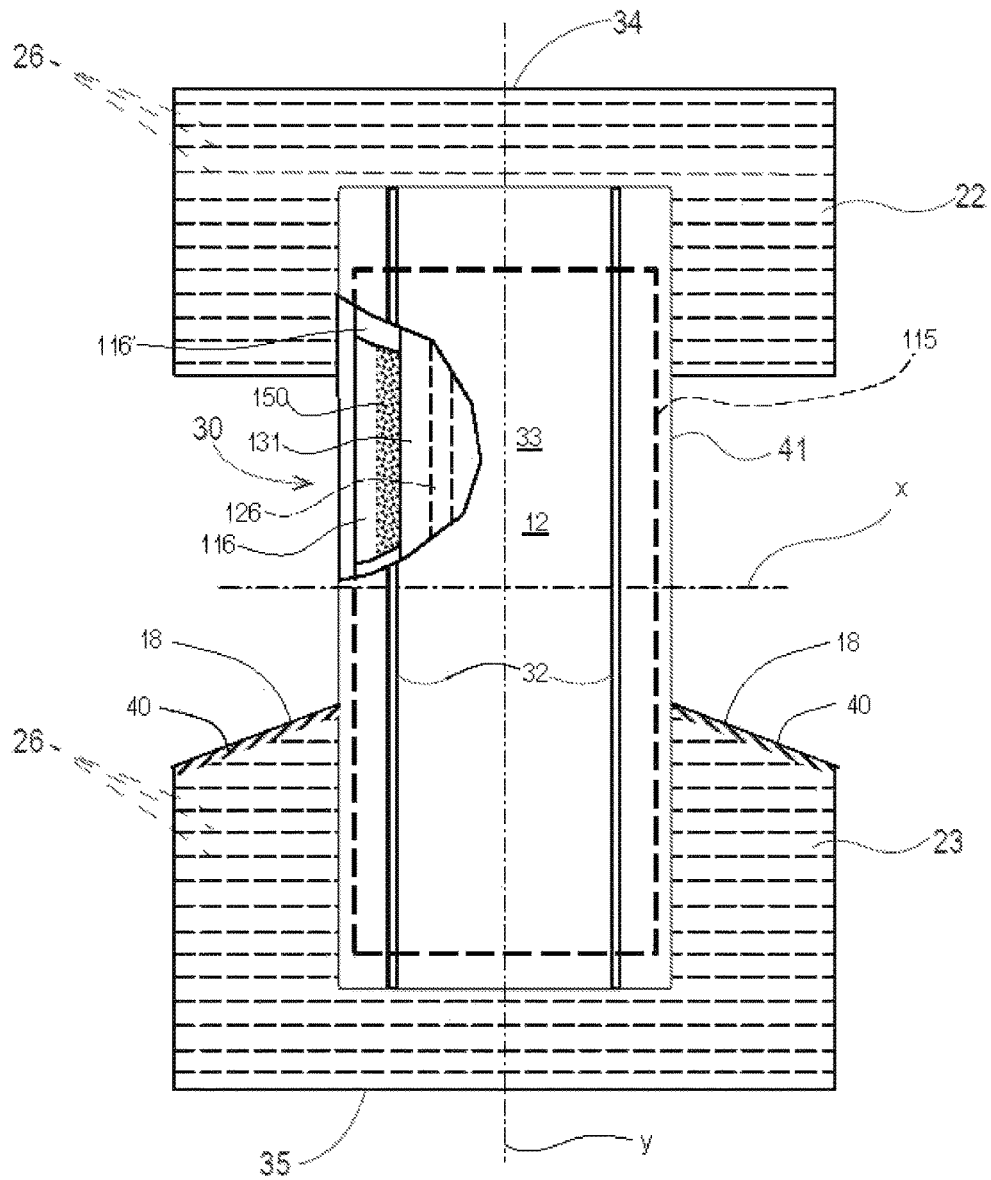
FIG. 2B is a schematic plan view of a balloon pant precursor structure, prior to joining of the front and rear belt portions at side seams, wearer-facing surfaces facing the viewer.
Figure 2C:
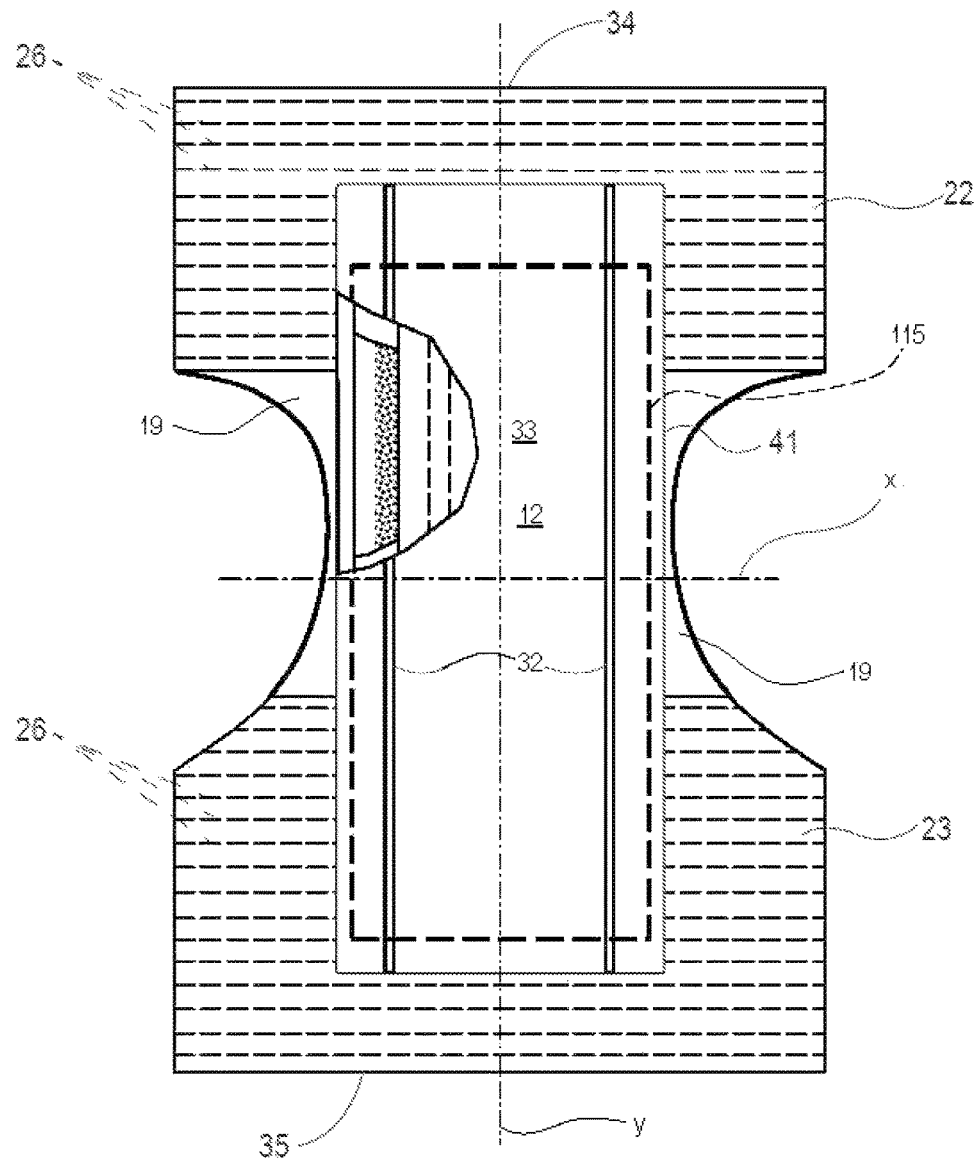
FIG. 2C is a schematic plan view of a balloon pant precursor structure, prior to joining of the front and rear belt portions at side seams, wearer-facing surfaces facing the viewer.

Referring to FIGS. 2A-2C, the "crotch region" of a pant is the portion through which the lateral axis (herein, axis x) passes, and which extends longitudinally one-sixth of the overall length of the pant frontward and rearward of the lateral axis. Accordingly, the front region includes the front one-third of the overall length of the pant; the crotch region includes the middle one-third of the length of the pant; and the rear region includes the rear one-third of the overall length of the pant.

As used herein "diapers" refers to devices which are intended to be placed against the skin of a wearer to absorb and contain the various exudates discharged from the body. Diapers are generally worn by infants and incontinent persons about the lower torso so as to encircle the waist and legs of the wearer. Examples of diapers include infant or adult diapers and disposable absorbent pants such as training pants and adult-incontinence pants.

"Disposable" is used herein to describe articles that are generally not adapted to be laundered or otherwise cleaned, restored or reused (i.e., they are only adapted to be durable enough to be used once, and then discarded, and may be recycled, composted or otherwise disposed of).

Throughout the present description, a material or composite of materials is considered to be "elastic" or "elastomeric" if, when a biasing force is applied to the material, the material or composite may be extended to an elongated length of at least 150% of its original relaxed length (i.e. can extend at least 50%), without rupture or breakage which substantially damages the material or composite, and when the force is removed from the material or composite, the material or composite recovers at least 40% of such elongation. In various examples, when the force is removed from an elastically extensible material, the material or composite may recover at least 60% or even at least 80% of its elongation.

"Elongation," used herein to quantify and express an amount of strain imparted to an elastic strand in the direction of its longitudinal axis, means: [(strained length of the strand−length of the strand before straining)/(length of the strand before straining)], ×100%. Where the term "pre-strain" is used to refer to elongation imparted to an elastic strand during manufacture of a belt structure or pant, it refers to elongation, expressed in the same manner.

"Film" means a macroscopically continuous skin-like or membrane-like layer of material formed of one or more polymers. "Film" is distinguished from "nonwoven web" or "nonwoven" in that the latter has a form consisting of a web-like structure of consolidated but predominately individually distinct fibers.

"Hot melt adhesive" as used herein refers to adhesives conforming with the description given in "Adhesion and Adhesives Technology: An Introduction" by Alphonsus V. Pocius (Hanser publishers Munich, 1997). Therein a hot melt is defined as an adhesive applied from the melt and gaining strength upon solidification.

"Lateral"—with respect to a pant and its wearer, refers to the direction generally perpendicular to the wearer's standing height, i.e., the horizontal direction when the wearer is standing. "Lateral" and "transverse" (and forms thereof) also refer to the direction perpendicular to the longitudinal direction. With respect to certain of the figures herein in which it is shown, the x-axis lies along the lateral and/or transverse direction.

"Longitudinal"—with respect to a pant and its wearer, refers to the direction generally parallel to the wearer's standing height, i.e., the vertical direction when the wearer is standing. "Longitudinal" is also the direction generally parallel to a line extending from the midpoint of the front waist edge, between the leg openings, to the midpoint of the rear waist edge of the pant, when the pant structure is separated at the side/hip seams and laid out unfolded, extended and flat. With respect to certain of the figures herein in which it is shown, the y-axis lies along the longitudinal direction.

Used to describe a feature, "longitudinally-oriented" means that the largest dimension of the feature has a longitudinal-direction vector component that is greater than its lateral-direction vector component. Conversely, "laterally-oriented" means that the largest dimension of the feature has a lateral-direction vector component that is greater than its longitudinal-direction vector component.

With respect to a pant, relative positional terms such as "lower," "lowest", "above," "below," "bottom," etc., and forms thereof, are expressed with respect to the vertically lowermost extent (in the crotch region) and uppermost extent (at the waist edges) of the pant structure along a vertical direction, when worn by a standing wearer. With respect to a precursor structure to the pant, the lowest portion is at the lateral axis (axis x depicted in the figures) and the highest portions are at the waist edges.

A "nonwoven" is a manufactured sheet or web of directionally or randomly oriented fibers which are first deposited and accumulated onto a moving surface (such as a conveyor belt) and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural and/or man-made origin and may be staple and/or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwovens may be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of a nonwoven is usually expressed in grams per square meter (gsm).

"Pant," as used herein, refers to a disposable absorbent garment having a waist opening, leg openings and an absorbent structure at least in the crotch region, adapted for wear by an infant, child or adult wearer. A pant may be placed in position on the wearer by inserting the wearer's feet into and through the waist opening and into the leg openings and sliding the pant up the wearer's legs into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

In the following description, a surface of a wearable absorbent article, or of a component thereof, which faces the wearer when worn, is called the "wearer-facing surface." Conversely, the surface facing away from the wearer is called the "garment-facing surface." Accordingly, a wearable absorbent article, and every sheet or web component thereof has a wearer-facing surface and a garment-facing surface.

"z-direction," with respect to a web, means generally orthogonal or perpendicular to the plane approximated by the web along the machine and cross direction dimensions.

Although examples of the structure of the invention are described herein as used to form the belt of a balloon-type absorbent pant, it will be appreciated that examples may be used to form other components of absorbent pants, diapers and other wearable articles (including disposable forms thereof), and other products as well.

Figure 1:
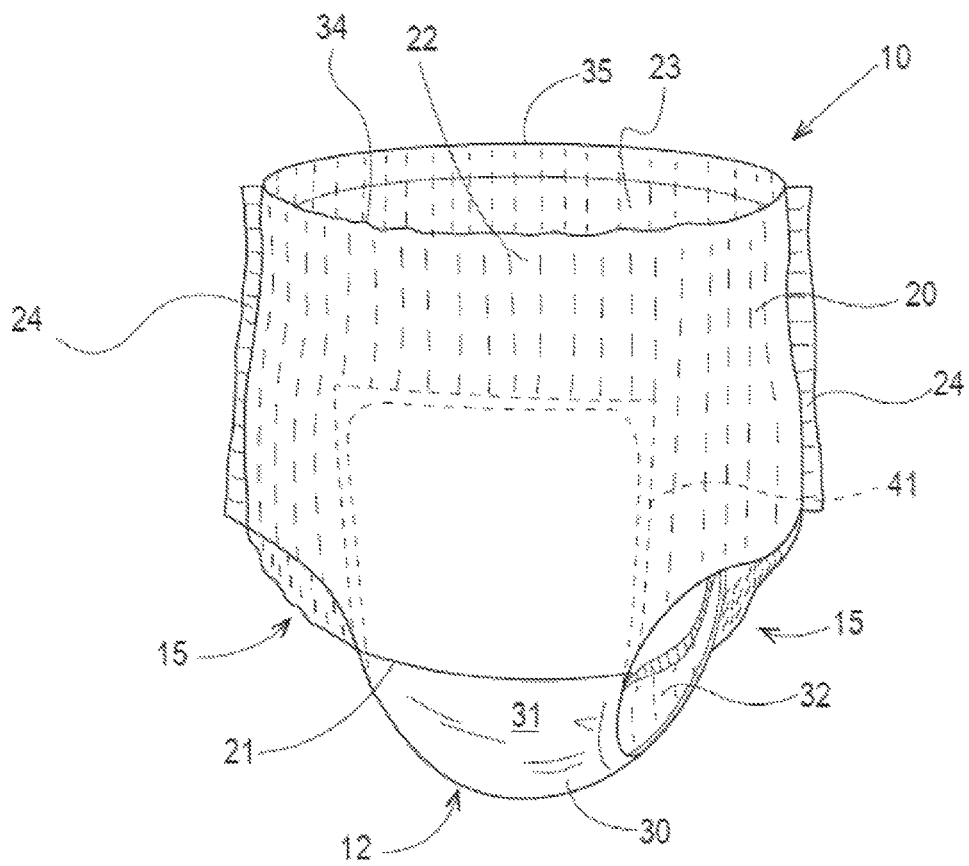
FIG. 1 is a front perspective view of an example of a balloon pant.

FIG. 1 depicts an example of balloon-type absorbent pant 10. FIGS. 2A-2C depict examples of the precursor structures of pants in an open configuration laid out flat and stretched out laterally against elastic-induced contraction, wearer-facing surfaces facing the viewer, prior to final assembly in which front belt portion 22 is joined to rear belt portion 23 at seams 24. To form pant 10, the precursor structure may be folded at or about lateral axis x (located at the longitudinal midpoint of the precursor structure) with the topsheet 33 facing inward, and the longitudinal edges of the front 22 and rear 23 belt portions may be joined at seams 24, forming a pant structure having leg openings 15, front waist edge 34 and rear waist edge 35.

The pant structure may include a belt 20 and a central chassis 30. Central chassis 30 may include any combination of components found in the absorbent structures of disposable diapers and absorbent pants, including but not limited to a liquid impermeable backsheet 31 formed at least in part of liquid impermeable web material, a liquid permeable topsheet 33, an absorbent core structure (described below), and elasticized barrier cuffs 32. Examples and descriptions of components and configurations of a central chassis may be found in U.S. Pat. App. Pub. No. 2013/0211355, as well as in the other references cited herein, to the extent not inconsistent herewith, wherein the chassis described includes components and features that may be included in central chassis 30. In the example shown in FIG. 1, the front portion of belt 20 stops short of the crotch region 12 of the pant, at lower edge 21. Central chassis 30 may overlie front and rear belt portions 22, 23 to the inside (wearer-facing side) thereof. The outer perimeter 41 of the central chassis 30 may be defined by the outer perimeter of the liquid impermeable web material.

Figure 16A:
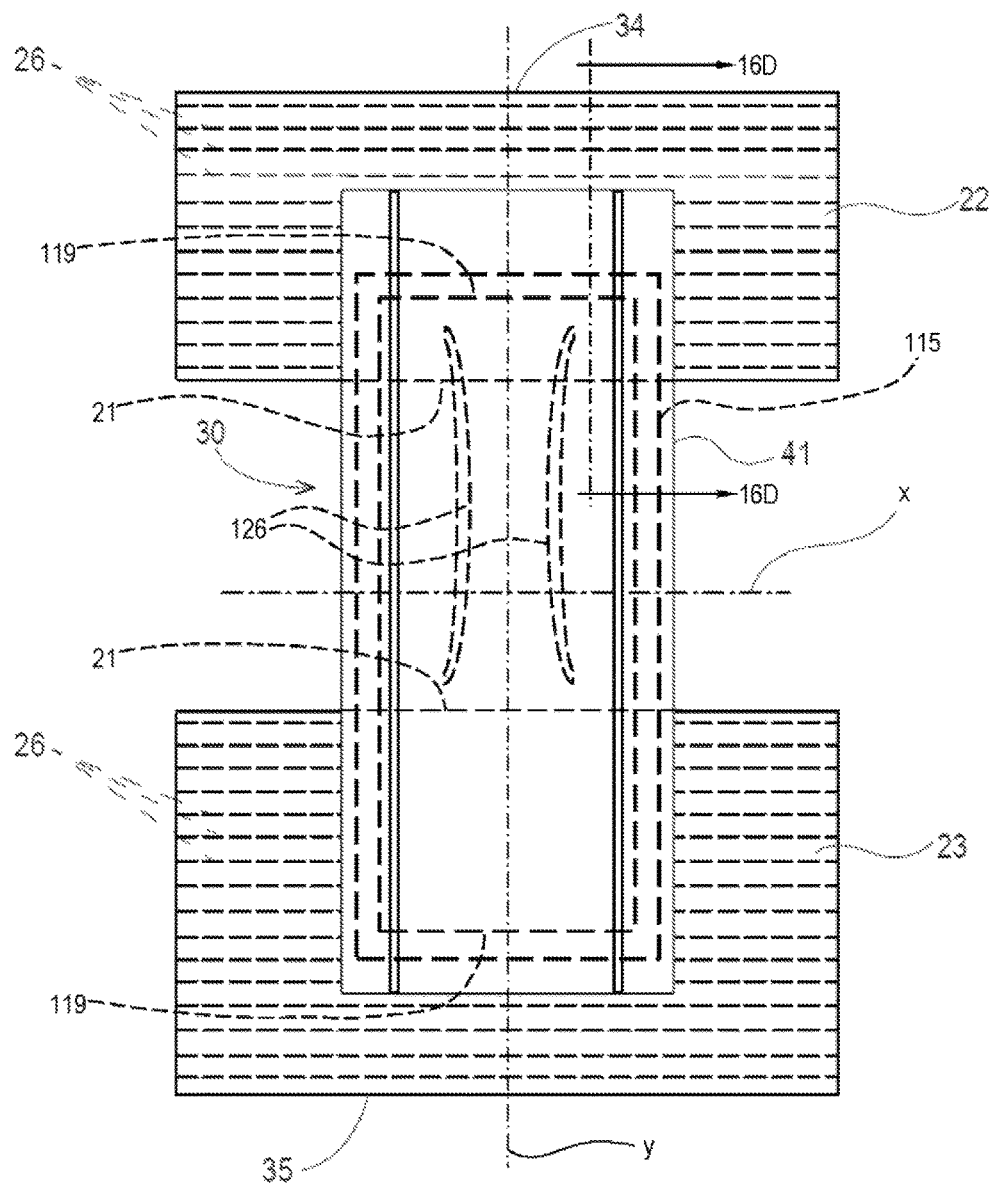
FIG. 16A is a schematic plan view of a non-limiting example of a balloon pant precursor structure, prior to joining of the front and rear belt portions at side seams, wearer-facing surfaces facing the viewer, shown with a configuration of longitudinal main channels.
Figure 16B:
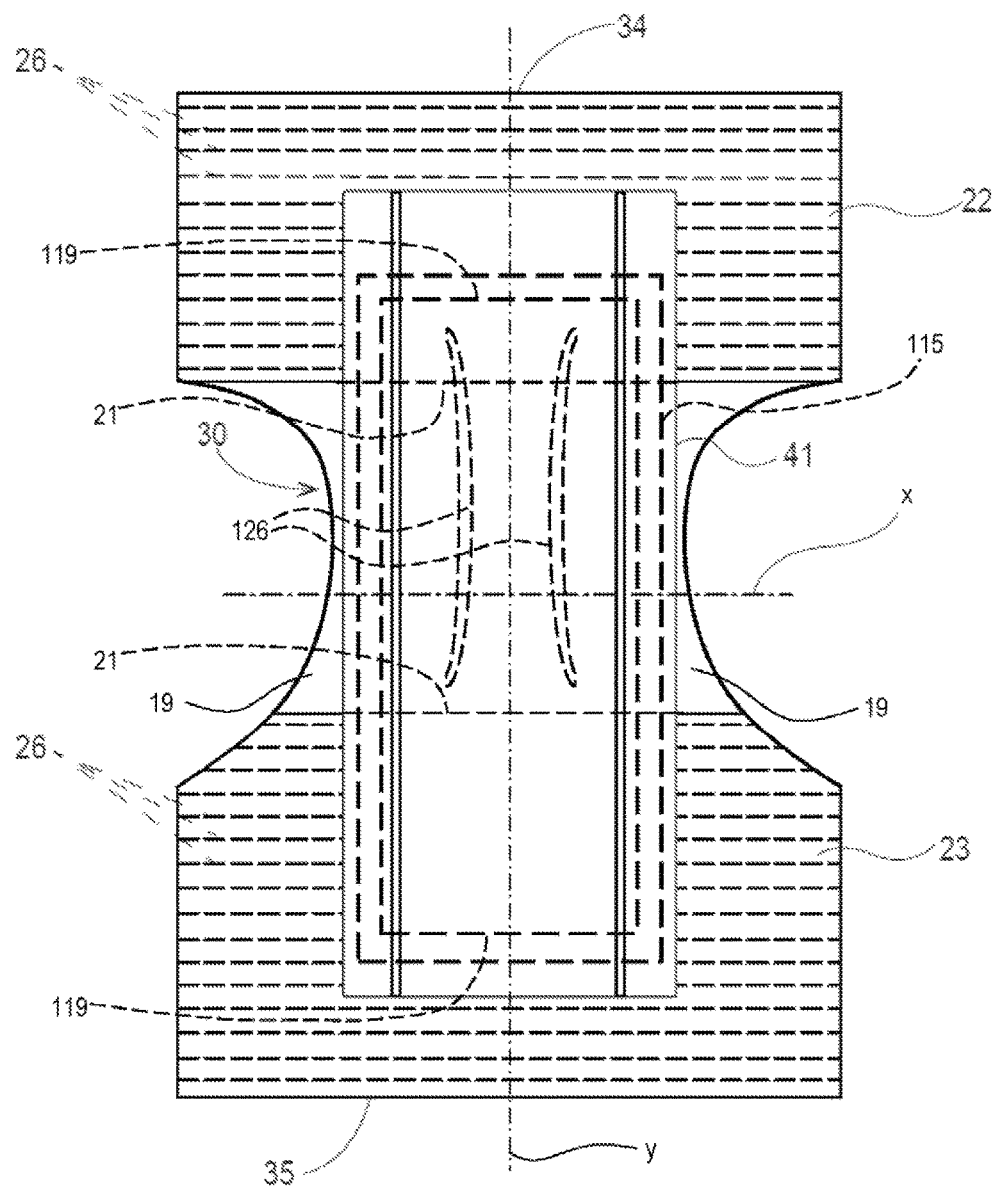
FIG. 16B is a schematic plan view of an alternate balloon pant precursor structure, prior to joining of the front and rear belt portions at side seams, wearer-facing surfaces facing the viewer, shown with a configuration of longitudinal main channels.

In the examples suggested in FIGS. 2A and 2B, front and rear belt portions 22, 23 may be the outermost structures forming the front and rear regions of the pant. In the example suggested in FIG. 2C (also as shown in FIG. 16B), the pant may include an outer wrap 19 wrapping the entirety of the front, crotch and rear regions, and forming an outermost pant-shaped/profiled structure. Additional layer(s) and elastic members to form front and rear belt portions 22, 23 may be disposed to the inside of outer wrap 19, and be suitably affixed thereto by adhesive lamination, bonding or any other suitable mechanism. An outer wrap 19 may be formed of one or more sections of nonwoven web, and as reflected in FIG. 2C, may be cut to a profile providing suitably tailored leg opening edge profiles as desired.

Figure 3:
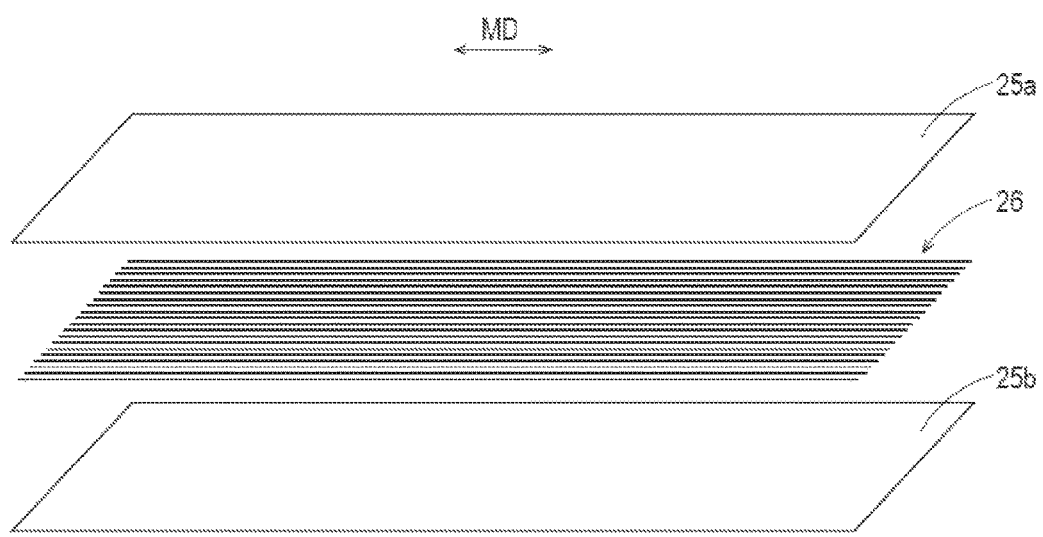
FIG. 3 is a schematic, exploded perspective view of components of a belt portion.
Figure 4:
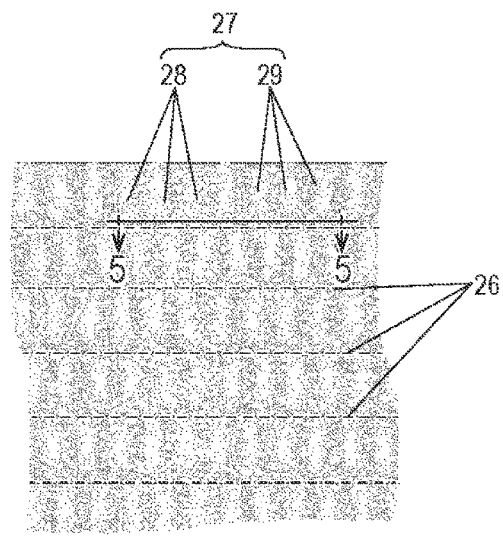
FIG. 4 is a schematic, close-up plan view of an area of a belt portion.
Figure 5:
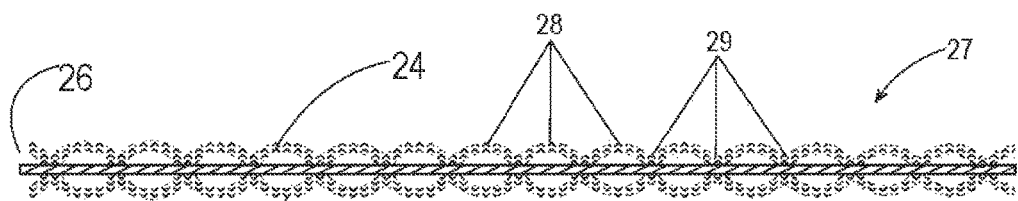
FIG. 5 is a schematic cross section of the area of the belt portion shown in FIG. 4.

Referring to FIGS. 3-5, one or both of front and rear belt portions 22, 23 may be formed of layers of nonwoven web 25a, 25b, which respectively form inner and outer layers. Suitable nonwoven web materials that may be useful in the present invention also include, but are not limited to spun-bond, spunlaid, meltblown, spunmelt, solvent-spun, electro-spun, carded, film fibrillated, melt-film fibrillated, air-laid, dry-laid, wet-laid staple fibers, and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, polypropylene (PP), poly-ethylene (PE), poly-lactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and 13/005,237.

The individual fibers of which nonwoven layers 25a and 25b are formed may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides or other biopolymers.

According to one example, the nonwoven may include a material that provides good recovery when external pressure is applied and removed. Further, according to one example, the nonwoven may include a blend of different fibers selected, for example from the types of polymeric fibers described above. In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one both layers 25a, 25b used to form the belt portions, because they can feel particularly soft to the touch (for wearer comfort on the inside and aesthetically pleasing feel on the outside) and are generally quite pliable, making them easily drawn laterally at the lower rear leg edges as will be described below.

Referring to FIGS. 3-5, layers of nonwoven web 25a, 25b may sandwich one or more elastic members such as a plurality of elastic strands 26. Elastic strands may be formed of an elastomeric material, such as an elastane (for example, LYCRA HYFIT fiber, a product of Invista, Wichita, Kans.). Layers of nonwoven web 25a, 25b may be joined together about elastic strands 26 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 26 are depicted in the figures.

The elastic members can also be formed from various other materials, such as but not limited to, rubbers, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, and other elastomeric materials known in the art, and combinations thereof. In some examples, the elastic members may be extruded strand elastics with any number of strands (or filaments). The elastic members can have a decitex ranging from 50 to 2000, or any integer value for any decitex value in this range, or any range formed by any of these integer values. The elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

Still referring to FIGS. 3-5, during manufacture of the belt structure, the elastic members such as elastic strands 26 may be pre-strained lengthwise by a desired amount as they are being incorporated into the belt structure. Upon subsequent relaxation of the belt, the elastic members such as elastic strands 26 will contract laterally toward their unstrained lengths. This causes the layers of nonwoven material 25a, 25b to gather and form ruffles or rugosities 27 having ridges 28 and valleys 29 generally transverse to the lengths of the elastic strands 26, and extending in the z-direction.

In another example, to adhere the components of the belt laminate, the elastic strands 26 themselves may be individually coated with adhesive ("strand coated") prior to incorporation into the belt laminate. Various coating methods and techniques, including strand coating methods and techniques, are shown for example in U.S. Pat. Nos. 5,340,648; 5,501,756; 5,507,909; 6,077,375; 6,200,635; 6,235,137; 6,361,634; 6,561,430; 6,520,237; 6,582,518; 6,610,161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as AVANCÉ, available from Bostik, Inc., Wauwatosa, Wis.

Figure 6A:
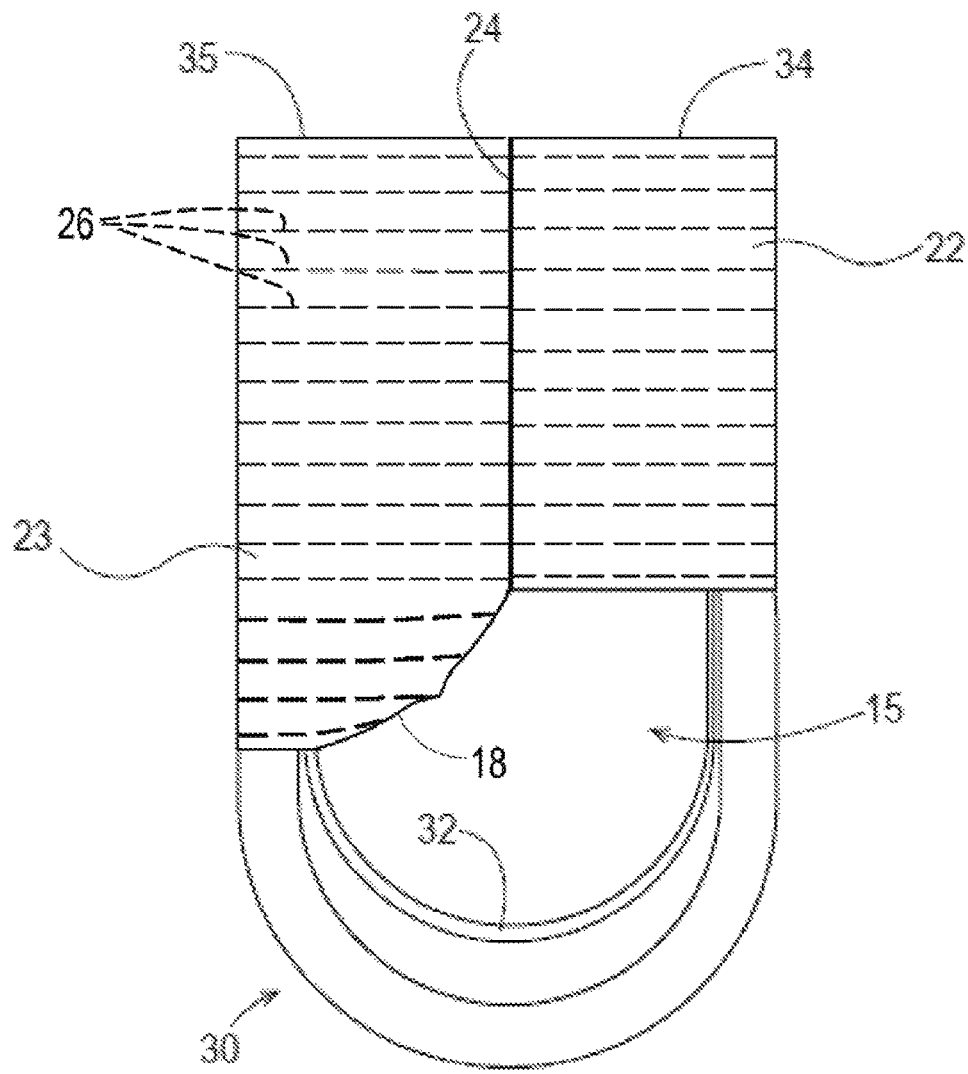
FIG. 6A is a schematic side view of a pant.

Referring to FIG. 2A, the rear belt portion 23 may have a greater longitudinal dimension (i.e., greater length) than the front belt portion 22. This may help provide greater coverage of the wearer's buttocks area in the rear while providing greater comfort in front, via better conformity with wearer anatomy and natural body movement. In the example of FIG. 2A, when the two portions 22, 23 are joined at side seams with their respective waist edges 34, 35 substantially aligned, however, the rear leg edges 18 will lie below the front leg edges to form a stepped leg edge profile at the seams. If deemed undesirable, this effect may be mitigated by selecting, disposing and/or varying pre-strain levels among the elastic members as suggested and described in, for example, U.S. Pat. App. Ser. No. 62/042,387, to laterally draw the lower rear corners of the rear belt portion inward toward the longitudinal axis y. A potential desirable result of such practice is schematically suggested in FIG. 6A.

Figure 6B:
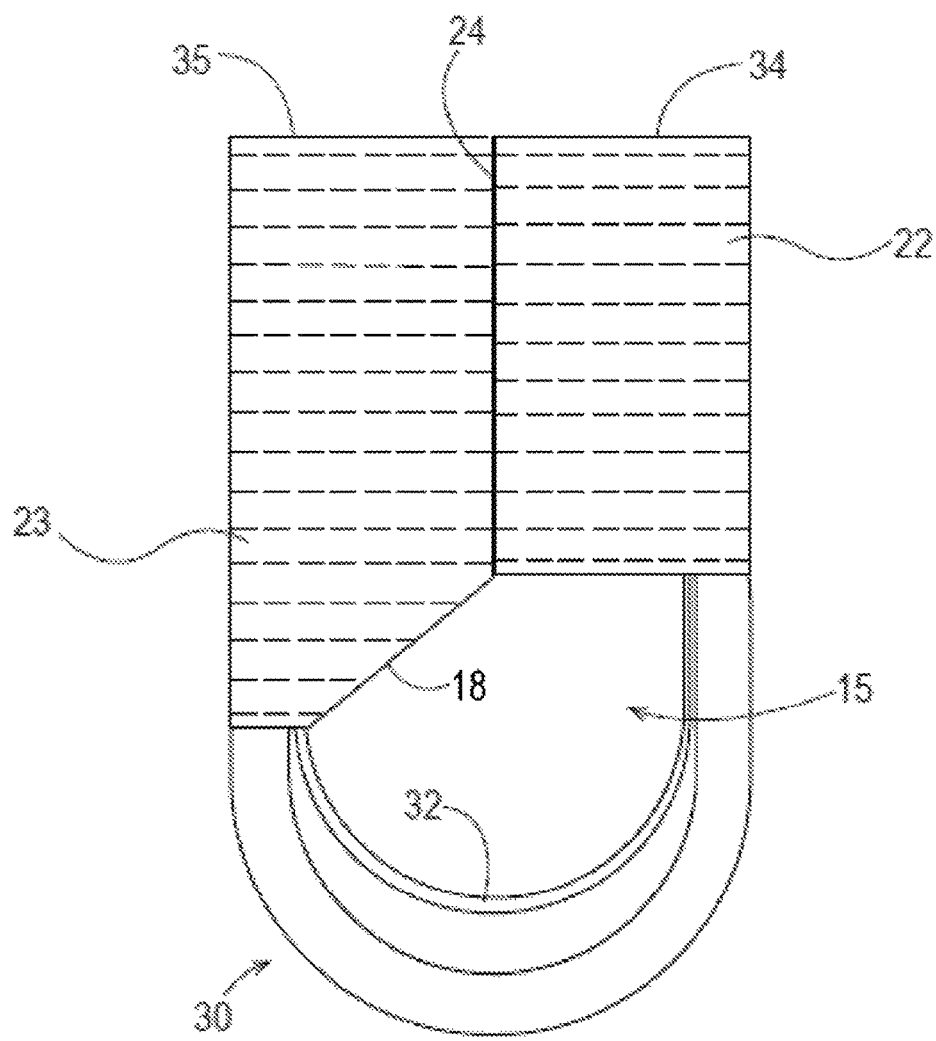
FIG. 6B is a schematic side view of a pant.

Alternatively, the lower rear corners of the rear belt portion may be trimmed off as suggested in FIGS. 2B and 6B. The lower rear corners may be trimmed off along straight lines as suggested in FIGS. 2B and 6B, or may be trimmed off along trim paths (not shown) that are curved and either concave or convex with respect to the remaining area of the rear belt portion 23, as may be desired to impart a particular curved rear leg edge profile. In conjunction with such trimming and the configuration of elastic strands described above, it may be desired to impart bonding 40 between layers 25a, 25b along edges 18 of rear belt portion 23. Such bonding may serve to prevent any separation of the layers along edges 18 that may contribute to creating a ragged appearance, and may also help the rear belt portion more effectively draw inward laterally toward the central chassis 30, under the contractive force of the elastic strands below seams 24. Bonding 40 may be effected by mechanical/compression bonds as described in, for example, U.S. Pat. Nos. 4,854,984 and 4,919,738, by thermal bonds or welds, or by deposits of adhesive between layers 25a, 25b. As suggested in FIG. 2B, such bonding may form a pattern along edges 18. Such bonding may be supplemental to any bonding between layers 25a, 25b generally holding rear belt portion 23 together as a laminate structure.

Side seams 24 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be effected. Bonding forming permanent seams may include compression bonding, thermal bonding/welds, ultrasonic bonding or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 24. Examples are depicted in U.S. Pat. App. Ser. Nos. 61/787,416; 61/787,332; 61/666,065.

Absorbent Structure

The absorbent structure 115 is a three-dimensional structure including a substrate layer 116 and an absorbent layer 117 including absorbent polymer particles, and optionally cellulose, supported by, and immobilized on, said substrate layer 116. Examples of absorbent structures 115 are illustrated in FIGS. 8, 10A, 10B, 14, 15A and 15B.

The substrate layer 116 of the absorbent structure may be any material capable of supporting the absorbent polymer particles. It may be a web or sheet material, such as foam, film, woven and/or nonwoven material.

Nonwoven materials and processes for making them are generally known in the art. Generally, processes for making nonwoven materials include two steps: depositing and accumulating fibers to the desired basis weight onto a forming surface, and consolidating and bonding the accumulated fibers to form a coherent web. The first step may include spunlaying, meltblowing, carding, airlaying, wetlaying, coforming and combinations thereof. The bonding step may include hydroentanglement, cold calendering, hot calendering, through air thermal bonding, chemical bonding, needle punching, and combinations thereof.

The nonwoven material may be a laminate. The laminate may include spunbond layer(s) (S), and/or meltblown layer(s) (M), and/or carded layer(s) (C). Suitable laminates include, but are not limited to, SS, SSS, SMS or SMMS. The nonwoven material may have a basis weight from about 5 to 100 gsm, or from about 8 to 40 gsm, or from about 8 to 30 gsm. Woven or nonwoven materials may include natural fibers or synthetic fibers or combinations thereof. The substrate layer 116 and the absorbent layer 117 may be coextensive or the substrate layer 116 may be slightly longer and wider than the absorbent layer 117 (as suggested in FIGS. 8, 10A, 10B, 14 and 15).

The absorbent layer 117 may include absorbent polymer particles 150, and optionally cellulose. The absorbent layer may include absorbent polymer in other forms such as absorbent polymer fibers. Absorbent polymer particles will be described in further detail below. The absorbent polymer particles may be used alone or in combination with other materials. In some examples, the absorbent layer includes absorbent polymer particles combined with cellulose. "Cellulose" as used herein refers to comminuted wood pulp in the form of fibers, sometimes also referred in the art as "air-felt". In some examples, the absorbent layer includes more than 70%, or more than 80%, or more than 90%, or more than 95% or even 100% by weight of absorbent polymer particles. In some other examples, the absorbent layer includes absorbent polymer particles and less than 5% by weight of cellulose, or less than 2% by weight of cellulose, or even substantially no cellulose. In examples wherein the absorbent layer is cellulose free, the only absorbent material in the absorbent layer is the absorbent polymer (particles, fibers, etc.). The resulting absorbent structures have a reduced thickness in the dry state compared to conventional absorbent structure including cellulosic fibers. The reduced thickness helps to improve the fit and comfort of the absorbent article for the wearer.

The absorbent layer 117 may include at least two main channels 126. Referring to FIGS. 2A, 2B and 8-14, "channels" as used herein refers to troughs or other identifiable elongate passageways through the deposit of absorbent polymer particles of the absorbent layer, partially or entirely extending through the z-direction thickness of the absorbent layer 117 and characterized by areas of comparatively reduced mass per unit spatial volume density of absorbent polymer particles in the space occupied by the absorbent structure, or even by areas that are substantially free of absorbent polymer particles, i.e. substantially no absorbent polymer particles are present in such volume (longitudinal channel or secondary channel) of an absorbent structure. The channels may have two shorter boundaries 128 (in the shortest dimension) at their ends and two longer boundaries 127 (in the longest dimension) along their sides, connecting the shorter boundaries. The shorter boundaries may be straight (e.g., perpendicular to the longer boundaries), or angled, or curved. The channels may have an average width w of at least 3 mm (the average width of a channel is defined as the average distance between the longer boundaries), or of at least 4% of the transverse width N of the absorbent layer.

The channels may be permanent. By permanent, it is meant that the integrity of the channels is substantially maintained both in dry state and wet state, i.e. the channels are substantially resistant to the effects of wetting (e.g., structure is maintained by materials that are insoluble in water), and substantially withstand mechanical stresses in the materials caused by swelling of absorbent polymer particles, pressure within the structure resulting therefrom, and the wearer's body movements. Permanent channels may be formed by immobilizing the absorbent polymer particles on the substrate layer, such as by applying a thermoplastic adhesive material over the absorbent layer. The absorbent layer of the present disclosure may also include permanent channels formed by permanently bonding of a first substrate layer (116) and a second substrate layer (116') together along the channels, thereby, in one example, forming chambers that separate and contain absorbent polymer particle deposits and thereby define the channels therethrough. Adhesive may be used to bond the substrate layers 116, 116' together along the channels, but it is possible to bond the substrate layers together via other means, for example, ultrasonic bonding, pressure bonding or thermal bonding. The supporting layers may be continuously bonded or intermittently bonded along the channels.

Figure 8:
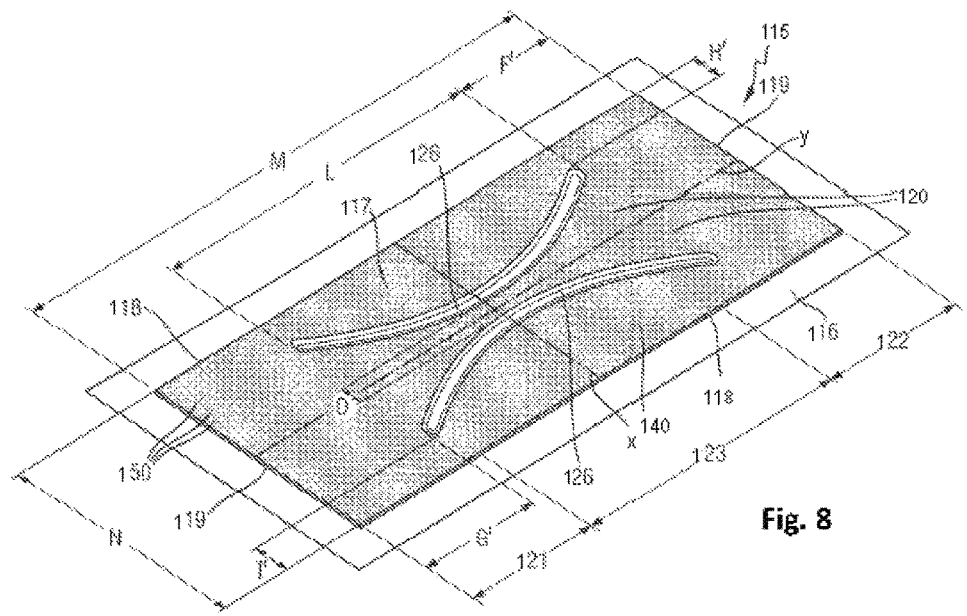
FIG. 8 is a schematic perspective view of an absorbent structure including an absorbent layer with two longitudinal main channels in accordance with one non-limiting example.
Figure 9:
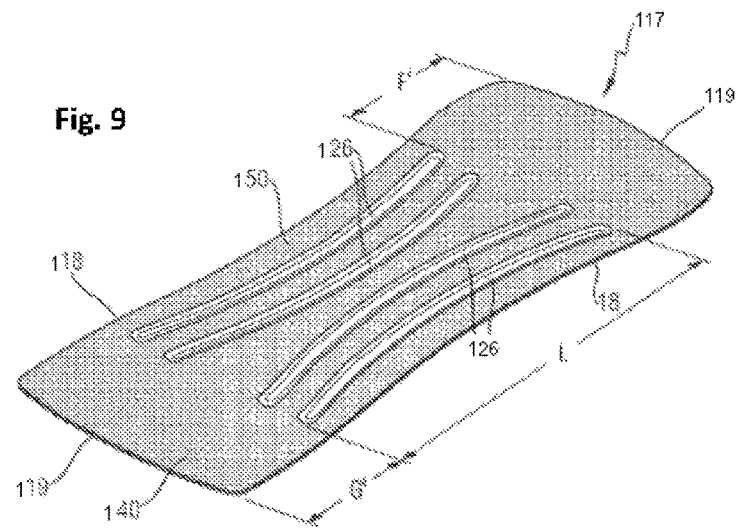
FIG. 9 is a schematic perspective view of an absorbent layer with four longitudinal main channels in accordance with one non-limiting example.

The absorbent layer may have two channels 126 located in the absorbent layer 117 such that the absorbent layer is divided by channels into three sections in the crotch region 123. As shown in FIGS. 2A, 2B and 8-10, the channels may be present in the crotch region of the absorbent layer. In some examples, the two channels may extend longitudinally along at least 15%, or at least 20% or at least 30% and up to 50%, or up to 70% or up 90% of the length M of the absorbent layer (i.e. they may extend over a distance L which is at least 15% and up to 50%, or up to 70% or up 90% of the length M of the absorbent layer). In some examples, the channels may be present only in the crotch region 123. When present only in the crotch region, the channels may extend over the whole longitudinal dimension of the crotch region, e.g. 50% of the length M of the absorbent layer, or they may extend in only part of the crotch region, i.e. from at least 15%, or at least 20% or at least 30% to 40%, or to 45% or to less than 50% of the length of the absorbent layer. In some examples, the channels 126 may be present in the crotch region, or part thereof, and part of the front region and/or part of the back region (such as shown in FIGS. 8-10). In some examples, the channels may be present in the front and crotch regions, i.e. the channels extend from the crotch region (or part thereof) into the front region. In some examples, the channels may be present in the back and crotch regions, i.e. the channels extend from the crotch region (or part thereof) into the back region. The channels 126 may be mirror images of one another with respect to the longitudinal axis y of the absorbent layer 117, i.e. the channel in one longitudinal region 120 may be mirror image of the longitudinal main channel in the other longitudinal region of the absorbent layer 117.

In some examples, it may be desired that the channels 126 do not extend all of the way to one or both of the transverse edges 119 (front and back) of the absorbent layer 117, i.e. from one transverse edge to the other. The absorbent layer may include, along each transverse edge and adjacent to said edge, an end deposit of absorbent polymer particles free of channels which extends in the transverse dimension of the absorbent layer from one longitudinal edge 118 of the absorbent layer 117, to the other. Such end deposits may have respectively a width F' or G' which are at least 5% of the longitudinal dimension of the absorbent layer (i.e. a width which is at least 5% of the length of the absorbent layer). In other words, the smallest distance F' or G' between the edge of a channel and the transverse edge of the absorbent layer is at least 5% of the longitudinal dimension M of the absorbent layer. In some examples, the width F' or G' is at least from 5% to 15%, or to 10% of the longitudinal dimension of the absorbent layer.

Furthermore, in order to reduce the risk of fluid leakage and run-off, it may be desired that the channels do not extend to the longitudinal edges 118 of the absorbent layer 117. The absorbent layer may include, along each longitudinal edge, a side deposit of absorbent polymer particles free of channels, which extends the length M of the absorbent layer from one transverse edge 119 to the other. Such side deposits may have respectively a width I' or H' which is at least 5%, or at least 10%, or at least 12% to 25% of the width N of the absorbent layer in a given region (i.e. a width I' or H' which is at least 5% of the width N of the absorbent layer). In other words, the minimum distance I' or H' between the edge of a channel and the longitudinal edge 118 of the absorbent layer is at least from 5% to 25% of the transverse dimension of the absorbent layer. For example, the distance I' or H' in the crotch region may correspond to at least 5%, or to at least 10% or at least 12% of the transverse dimension N of the absorbent layer in said crotch region. In some examples, the distance I' and/or H' is of 10 mm, or 15 mm or 20 mm.

Figure 10A:
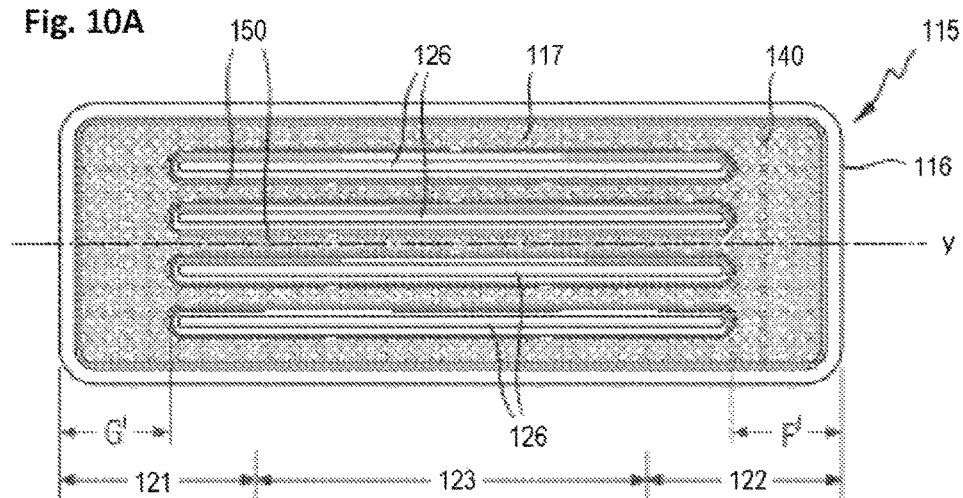
FIG. 10A is a schematic top/plan view of an absorbent structure including an absorbent layer with four longitudinal main channels in accordance with one non-limiting example.
Figure 10B:
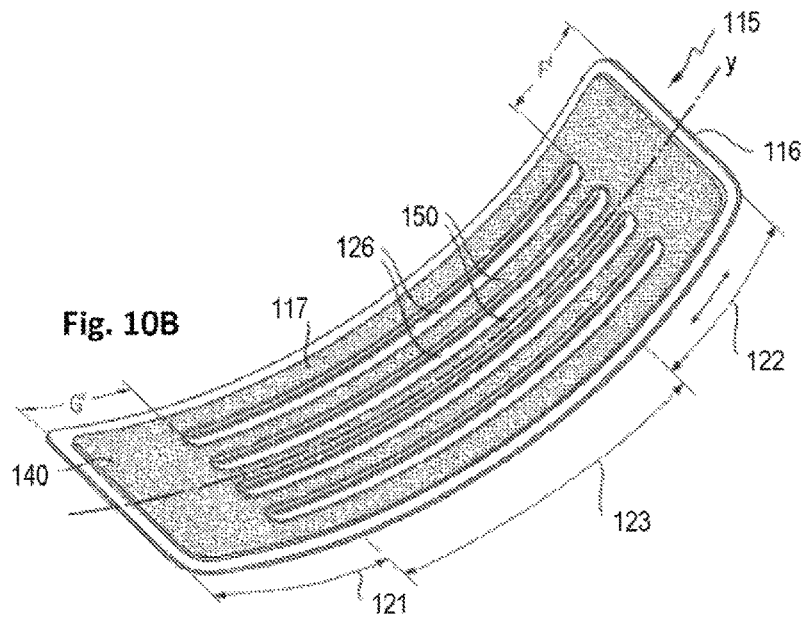
FIG. 10B is a schematic perspective view of the absorbent structure of FIG. 10A, shown in a flexed position.
Figure 11A:
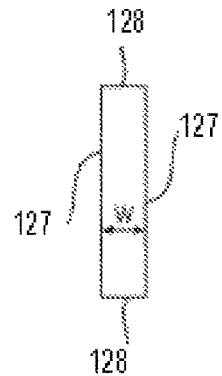
FIGS. 11A to 11E are schematic plan view representations of channel configurations in accordance with various non-limiting examples.
Figure 11B:
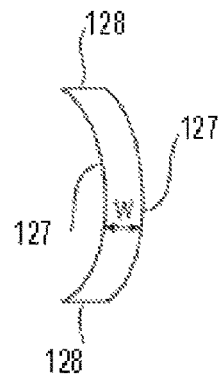

The channels may be substantially straight, and may run substantially parallel to the longitudinal axis y of the absorbent layer (as shown schematically in FIGS. 10A, 10B and 11A). Straight channels may serve as hinge structures in the absorbent structure, which may help enable the absorbent structure to flex longitudinally and thereby better conform to the wearer's anatomy along the transverse direction through the crotch region, and may also help enable the absorbent structure to form a containing shape better suited to receiving and containing liquid exudate before it is completely absorbed, when the pant is worn. Longitudinally extended channels also may help improve fluid transportation and distribution along the length of the deposits of absorbent polymer particles within the absorbent structure, and thereby may help speed liquid absorption.

Alternatively, the channels may be curved and/or arcuate, as suggested in FIGS. 8, 9, 12 and 13. Longitudinally extended but curved channels may also serve as hinge structures in the absorbent structure which may help enable the absorbent structure to flex longitudinally and thereby conform to the wearer's anatomy along the transverse direction in the crotch region. Thus, the channels may contribute to imparting a comfortable and superior fit in addition to permitting improved liquid transportation and distribution.

Figure 11C:
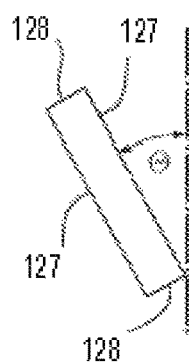
Figure 12:
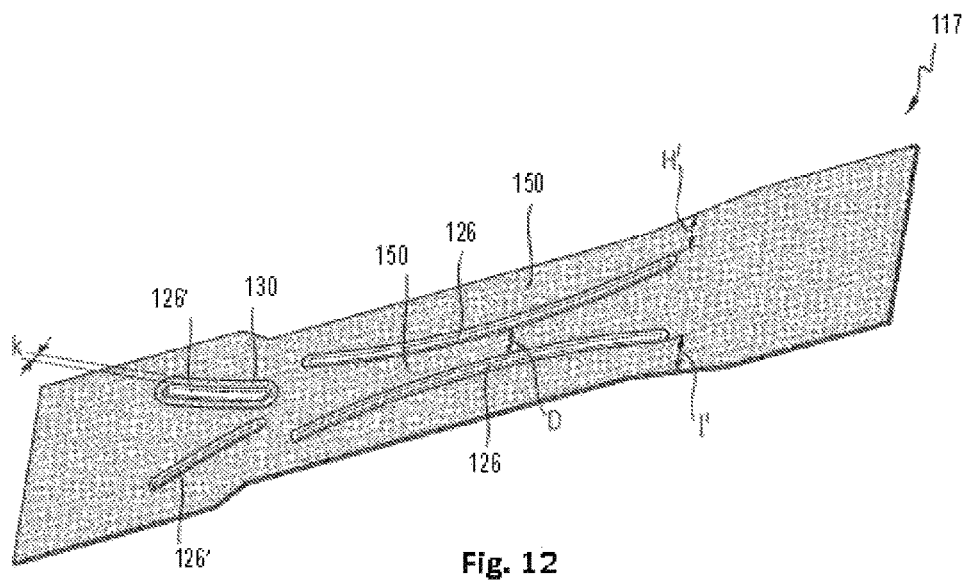
FIG. 12 is a schematic perspective view of an absorbent layer including two longitudinal main channels in the crotch region and two secondary channels in the front region in accordance with one non-limiting example.
Figure 13:
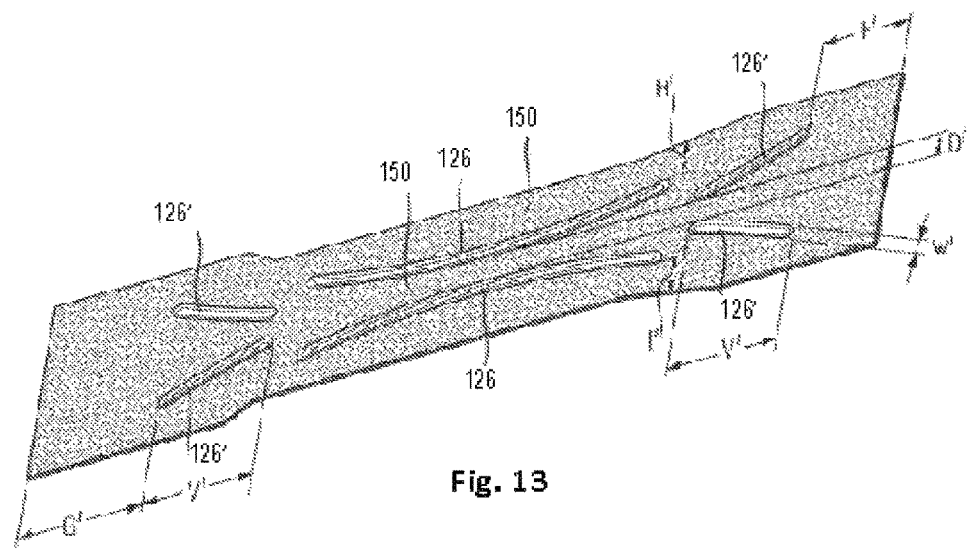
FIG. 13 is a schematic perspective view of an absorbent layer including two longitudinal main channels in the crotch region, two secondary channels in the front region and two secondary channels in the back region in accordance with one non-limiting example.
Figure 14:
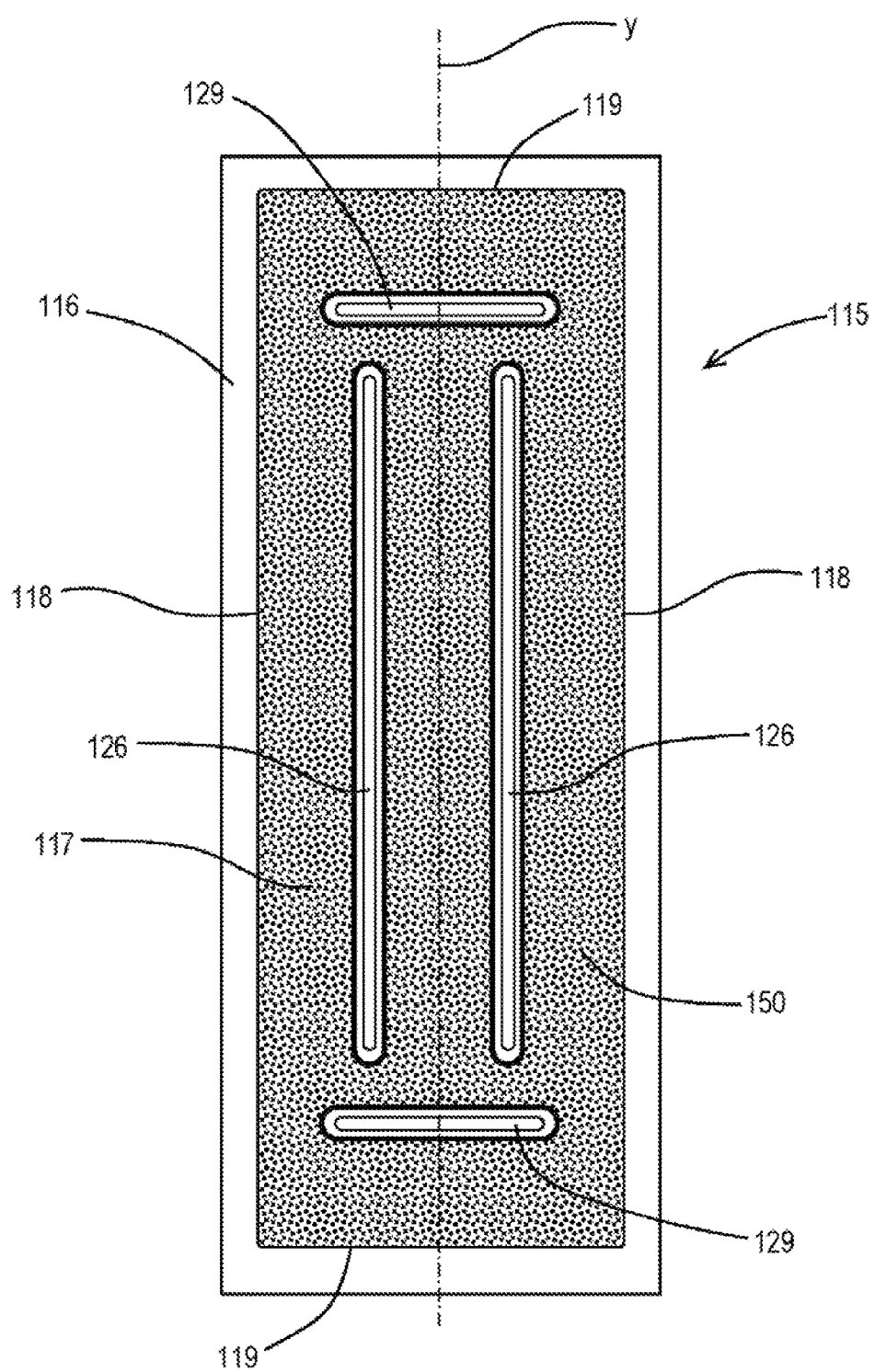
FIG. 14 is a schematic top/plan view of an absorbent structure with absorbent layer including two longitudinal main channels in the crotch region, and two secondary channels at front and rear, in accordance with one non-limiting example.
Figure 15A:
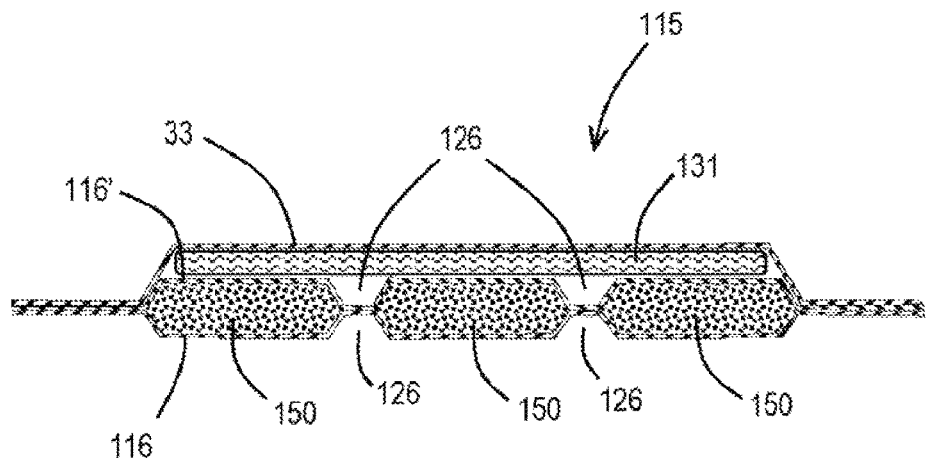
FIG. 15A is a schematic lateral cross-section view of an absorbent structure with longitudinal channels in accordance with one non-limiting example.
Figure 15B:
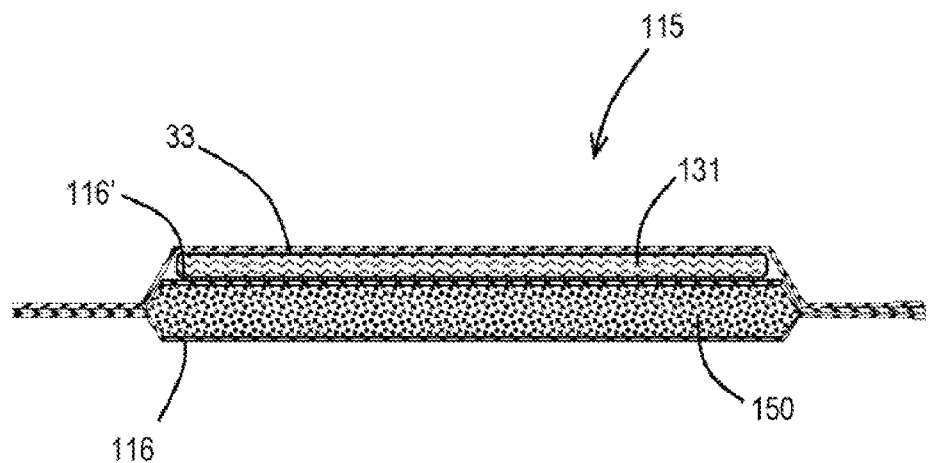
FIG. 15B is a schematic lateral cross-section view of an absorbent structure in accordance with one non-limiting example.

The channels 126 may include oblique channels, as suggested in FIGS. 11C, 12 and 13, i.e., substantially straight channels oriented at an angle θ of up to 30 degrees, or up to 20 degrees, or up to 10 degrees with respect to the longitudinal central axis y of the absorbent structure.

Figure 11D:
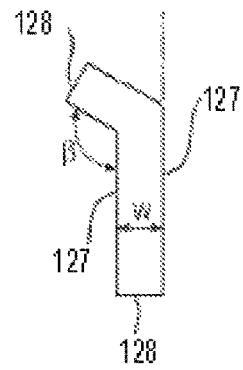
Figure 11E:
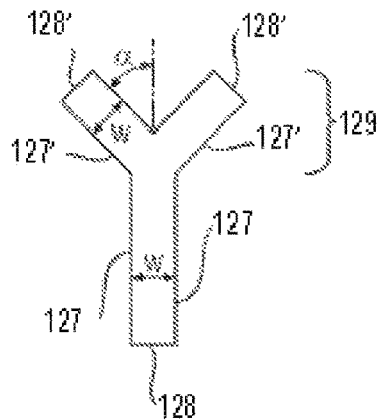

In some other alternatives, the channels may be angled channels, as suggested in FIG. 11D. Angled channels are channels made of two or more portions connected under an angle σ to one another. Angled channels may be made of two portions connected under an angle β of at least 150 degrees, or at least 160 degrees or at least 170 degrees.

The channels 126 may have an average width w of from 3 mm to 15 mm, or from 4 mm to 14 mm or from 5 mm to 12 mm (the average width of a channel is the average distance between its longer boundaries 127). The average width of the channels may be at least 4% of the width of the absorbent layer, or at least 7% and up to 15%, or 20% or 25%. In some examples, the channels may have an average width w of from 3 mm to 18 mm, or from 5 mm to 15 mm or from 6 to 10 mm.

The channels 126 may be separated in the crotch region by a distance D (illustrated in FIG. 8) of at least 5%, or at least 10%, or at least 20%, or at least 25% of the transverse dimension (width) of the absorbent layer in said crotch region. It is believed that when these two channels are separated by a distance of at least 5% of the transverse dimension of the absorbent layer in the crotch region, the absorbent structure is more likely to conform to the wearer's anatomy along the transverse direction and form a containing structure in the crotch region when the pant is worn. In some examples, the channels may be separated in the crotch region by a distance of at least 10 mm, or at least 15 mm, or at least 20 mm, or at least 30 mm. In some examples, the distance separating the channels in the crotch region is from 20 to 30 mm.

Figure 7:
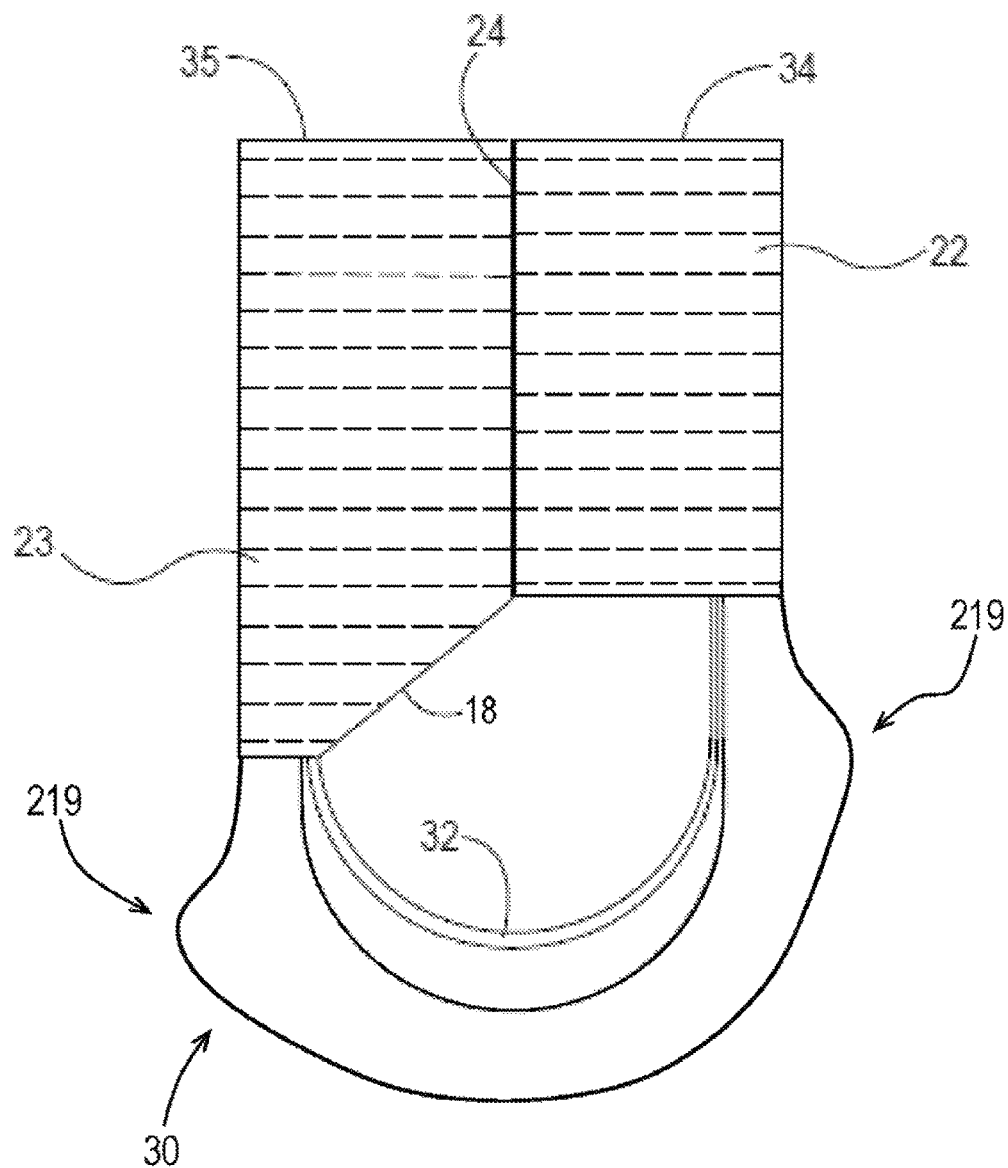
FIG. 7 is a schematic side view of a pant, shown in one configuration as loaded with absorbed liquid.

Longitudinally-oriented channels formed in the absorbent layer may help transport and distribute liquid (e.g., urine) along the lengths of the deposits of absorbent polymer particles in the absorbent layer, and thereby help speed acquisition and absorption. However, the correspondingly-defined longitudinal chambers or other structures containing or defining the deposits of absorbent polymer particles may develop elevated internal pressure as the particles absorb liquid, swell, and press against each other. This pressure may have a longitudinal, structural stiffening effect on the absorbent structure. The internal pressure causes the absorbent layer to tend to straighten longitudinally, rather than easily curve around and beneath the wearer's lower torso as the absorbent structure wraps between the wearer's legs. This stiffening effect may help prevent creation of a droopy or saggy appearance of the article when wetted. On the other hand, it has been discovered, as schematically illustrated in FIG. 7, this stiffening effect can cause the frontward and rearward ends of the absorbent structure to bulge away from the wearer's body in frontward and rearward directions, creating noticeable, unsightly, and potentially uncomfortable bulges 219 proximate the frontward and rearward ends of the absorbent layer. It has been discovered that this effect may be mitigated by one or more of several alternative configurations in a pant structure.

As suggested in FIGS. 12 and 13, the absorbent layer may include additional secondary channels 126' to further increase the fluid transportation and/or fit of the absorbent article. The above description of channels may equally apply to any of said secondary channels 126'. However, in some examples, the secondary channels may be shorter than the channels described above.

The longitudinal secondary channels may extend over a distance V' of at least 10%, or at least 15%, or at least 20% of the longitudinal dimension M of the absorbent layer (as illustrated in FIG. 13). They may extend up to 90% of the longitudinal dimension of the absorbent layer. The longitudinal secondary channels may extend up to 30% or 45% of the longitudinal dimension of the absorbent layer.

The absorbent layer may include one or more secondary channels, such as two, three, four, five or six. Secondary channels may be present in the front region, back region and/or crotch region of the absorbent layer. The absorbent layer may include an even number of secondary channels. The secondary channels may be distributed in the absorbent layer such that each longitudinal region of the absorbent layer includes an equal number of secondary channels. In some examples, the longitudinal regions including the channels (i.e. main longitudinal channels and secondary channels) are mirror images of each other with respect to the central longitudinal axis of the absorbent layer.

As suggested in FIGS. 14 and 17-19, in other examples the absorbent layer also may include one or more transverse secondary channels 129. Transverse channels 129 may have their longer dimensions oriented predominately in the transverse direction, or even be substantially perpendicular to the longitudinal axis y of absorbent layer 117. Transverse channels may serve as transverse hinge structures that can enable the absorbent structure to flex laterally and thereby conform to the wearer's anatomy along the longitudinal direction as it wraps around and beneath the wearer's lower torso between the legs from front to back. This may help mitigate the longitudinal stiffening effects of channels as illustrated in FIG. 7.

Figure 17:
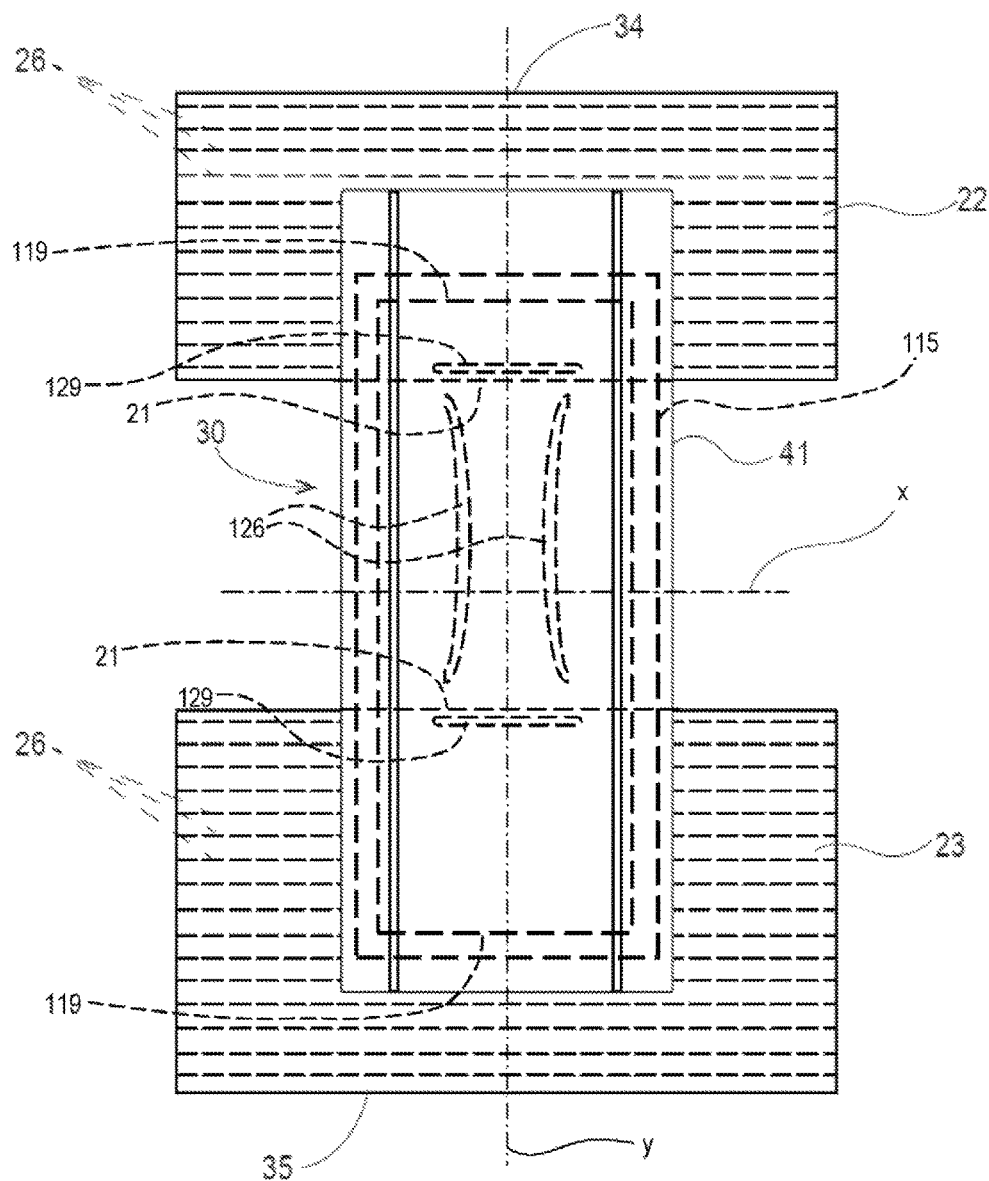
FIG. 17 is a schematic plan view of an alternate balloon pant precursor structure, prior to joining of the front and rear belt portions at side seams, wearer-facing surfaces facing the viewer, shown with another configuration of longitudinal main channels and secondary channels.
Figure 18:
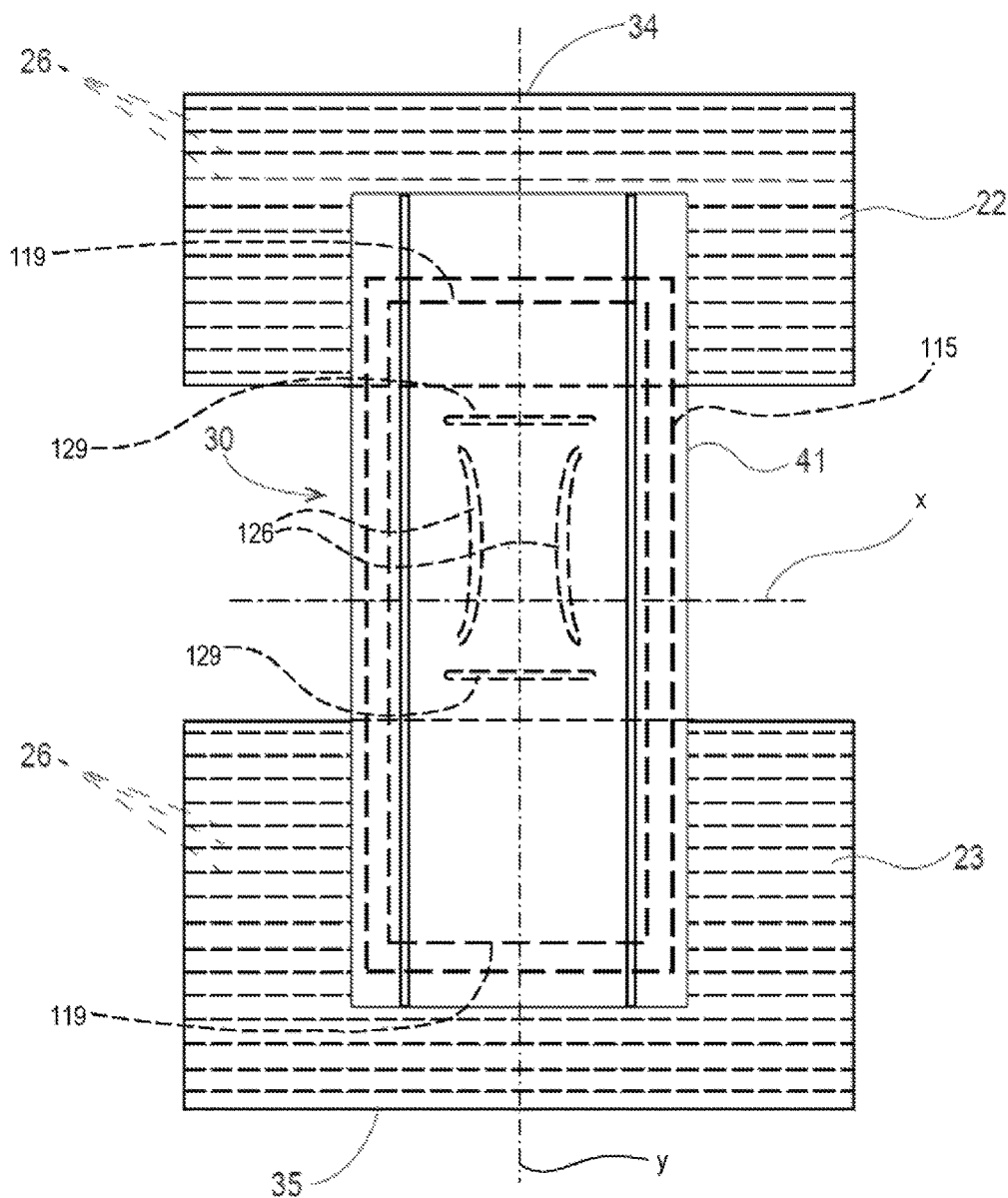
FIG. 18 is a schematic plan view of an alternate balloon pant precursor structure, prior to joining of the front and rear belt portions at side seams, wearer-facing surfaces facing the viewer, shown with another configuration of longitudinal main channels and secondary channels.
Figure 19:
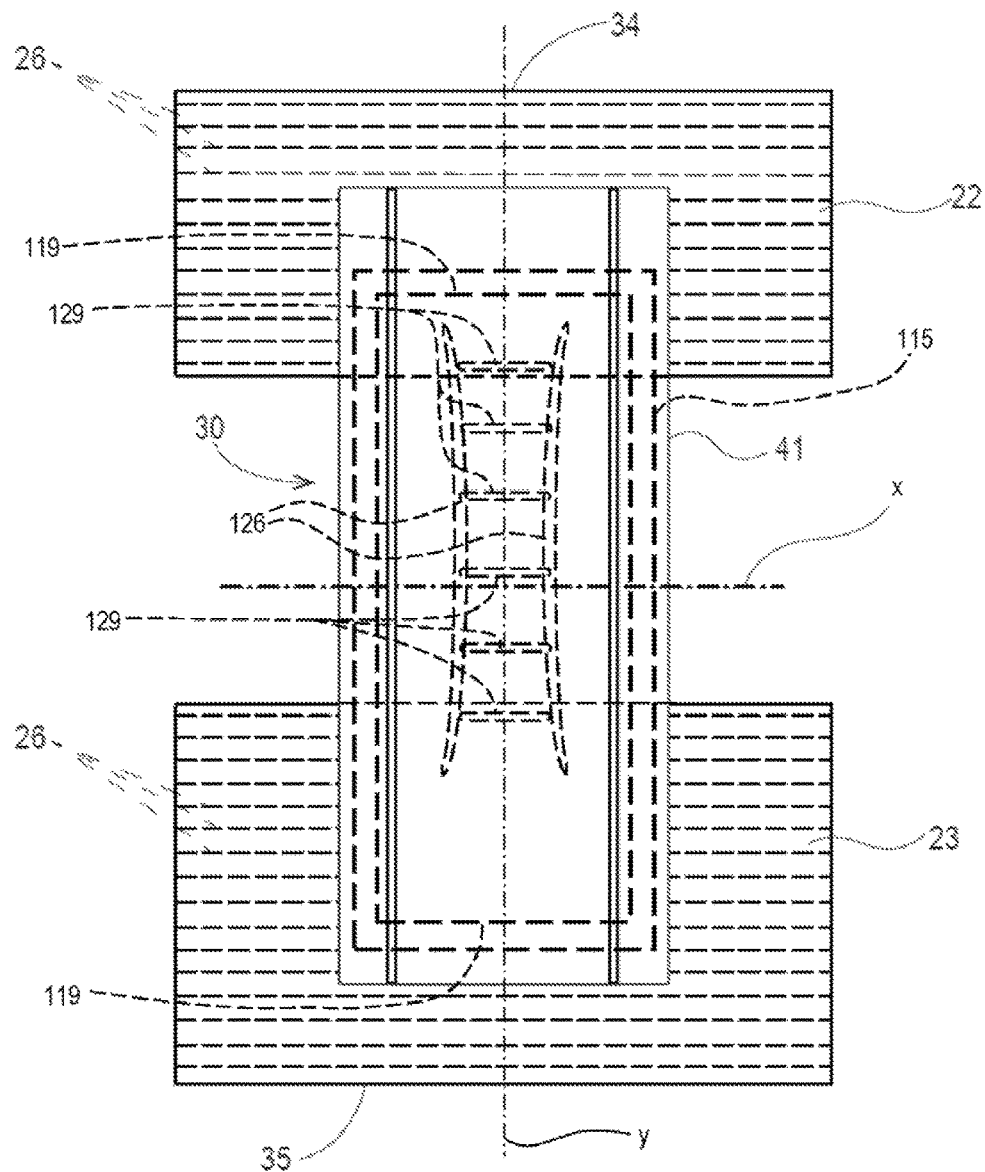
FIG. 19 is a schematic plan view of an alternate balloon pant precursor structure, prior to joining of the front and rear belt portions at side seams, wearer-facing surfaces facing the viewer, shown with another configuration of longitudinal main channels and secondary channels.

Transverse channels may be disposed above the lower edge 21 of the belt (FIG. 17), or below it (FIG. 18), although for better appearance and control of the shape of the loaded absorbent layer, when only one or two transverse channels are present, it may be preferred that one or both be disposed above the lower edge of the belt (as suggested in FIG. 17). In alternative examples, one or more transverse channels may be disposed between the lateral axis x and the lower edge 21 of the front belt portion and/or the rear belt portion.

Transversely-oriented secondary channels 129 may extend over a distance of at least 10%, or at least 15%, or at least 20%, of width N of the absorbent layer. They may extend up to 90% of the transverse dimension of the absorbent layer. The transverse secondary channels 129 may extend up to 30% or 45% of the transverse dimension of the absorbent layer. In some examples, transverse channels 129 may connect main channels 126, as suggested in FIG. 19. In some examples, transverse channels 129 may be distinct and separate from main channels 126, as suggested in FIGS. 14, 17 and 18.

The channels may be sized and located in the absorbent layer such that a central deposit of absorbent polymer particles extending along the central longitudinal axis of the absorbent layer (and including said axis) from one transverse edge to the other one, and having a width D' of at least 5%, or at least 10% and up to 60%, or up to 70%, or up to 75% of the transverse dimension of the absorbent layer remains free of channels. The absorbent polymer particles may be substantially continuously present in such a central deposit. For example, a central deposit may have a width D' of at least 5 mm, or at least 10 mm, or at least 15 mm or 20 mm and up to 70 mm or up to 40 mm. The absence of channels in such a central deposit is advantageous since it at least inhibits the diaper from taking an inverted V-shape configuration (along the transverse direction) in the crotch region when the pant is worn. An inverted V-shape configuration may increase the risk of liquid leakage along the leg openings. In some examples, the average basis weight of absorbent polymer particles in such a central deposit is relatively high, i.e. at least 350 gsm and up to 1000 gsm, or for example from 450 gsm to 750 gsm, and higher than the basis weight at other locations of the absorbent layer.

In other examples, the absorbent layer structure defining the channels 126 and corresponding longitudinally-oriented volumes containing deposits of absorbent polymer particles may be imparted with features that cause the structure to change from a first configuration when dry to a second configuration when wetted to, e.g., one-quarter, one-third, one-half, two-thirds or more of the total absorbent capacity (by weight of absorbed liquid) of the absorbent layer. For example, materials used to form longitudinal chambers or other structures containing or defining correspondingly longitudinally-oriented deposits of absorbent polymer particles, and defining channels among/between them, may be configured to change structure when wetted. In one example, illustrated with reference to FIGS. 15A and 15B, an absorbent structure 115 may have a first configuration when dry (e.g., FIG. 15A) and a second configuration when wetted (e.g., FIG. 15B), e.g., to more than half of its absorbent capacity. One mechanism that may be used to enable this may be a water soluble or otherwise releasable adhesive affixing substrate layers 116 and 116' together along, and thereby defining, channels 126. Upon wetting and/or outward pressure against layers 116 and 116' from the swelling deposits of absorbent polymer particles, the adhesive releases, and the swelling deposits of absorbent polymer particles are permitted to expand into the volume previously defined by the channels 126, which then may reduce in size or even disappear as suggested in FIG. 15B. This may have the effect of relieving pressure within the absorbent layer 117 and absorbent structure 115, which may lessen the longitudinal stiffening effects described above. Thus, advantages of channels (flexibility, conformability and liquid distribution enhancement) may be enjoyed at times before the pant is substantially wetted, while a disadvantage of channels (longitudinal stiffness) may be mitigated at times after the pant has been substantially wetted.

This changing channel structure may be utilized alone or may be combined with permanent channel structures of any desired configuration, including but not limited to any configuration described herein.

In a further example, main channels 126 may have a length in the longitudinal direction. The length may be divided into three, four, five or more sublengths. The structure defining the channels may be configured to permanently define the channels along one or more of the sublengths, but to changeably define the channels along other of the sublengths, such that they reduce in size or disappear upon wetting. In one example, channels are permanently defined in areas proximate the lateral axis x of the pant, and are changeably/releaseably defined, e.g., as described above, in areas further away from the lateral axis x. In some examples, one or more sublengths at and/or proximate the ends of the channels are changeable/releaseable upon wetting. In one particular example, one or more longitudinal main channels 126 are divided into five sublengths. The intermediate sublength may be permanently defined, while the two sublengths toward each end of the channel may be changeably/releaseably defined such that they reduce in size or disappear upon wetting as described above. In alternative examples including one or more longitudinally oriented channels, a portion of the channel(s) may be permanent and a portion of the channel(s) may be temporary or releasable. The temporary portions of the channel(s) may be disposed between the lateral axis x and a lower edge 21 of the belt. In some examples the temporary portion of the channel may be disposed at one or both of the ends of the channel and may occupy between 10 and 25% of the dry length of the channel at one or both ends. The temporary portions of the channel may also be disposed intermittently along the length of the channel and may alternate with permanent portions of the channel.

Figure 16C:
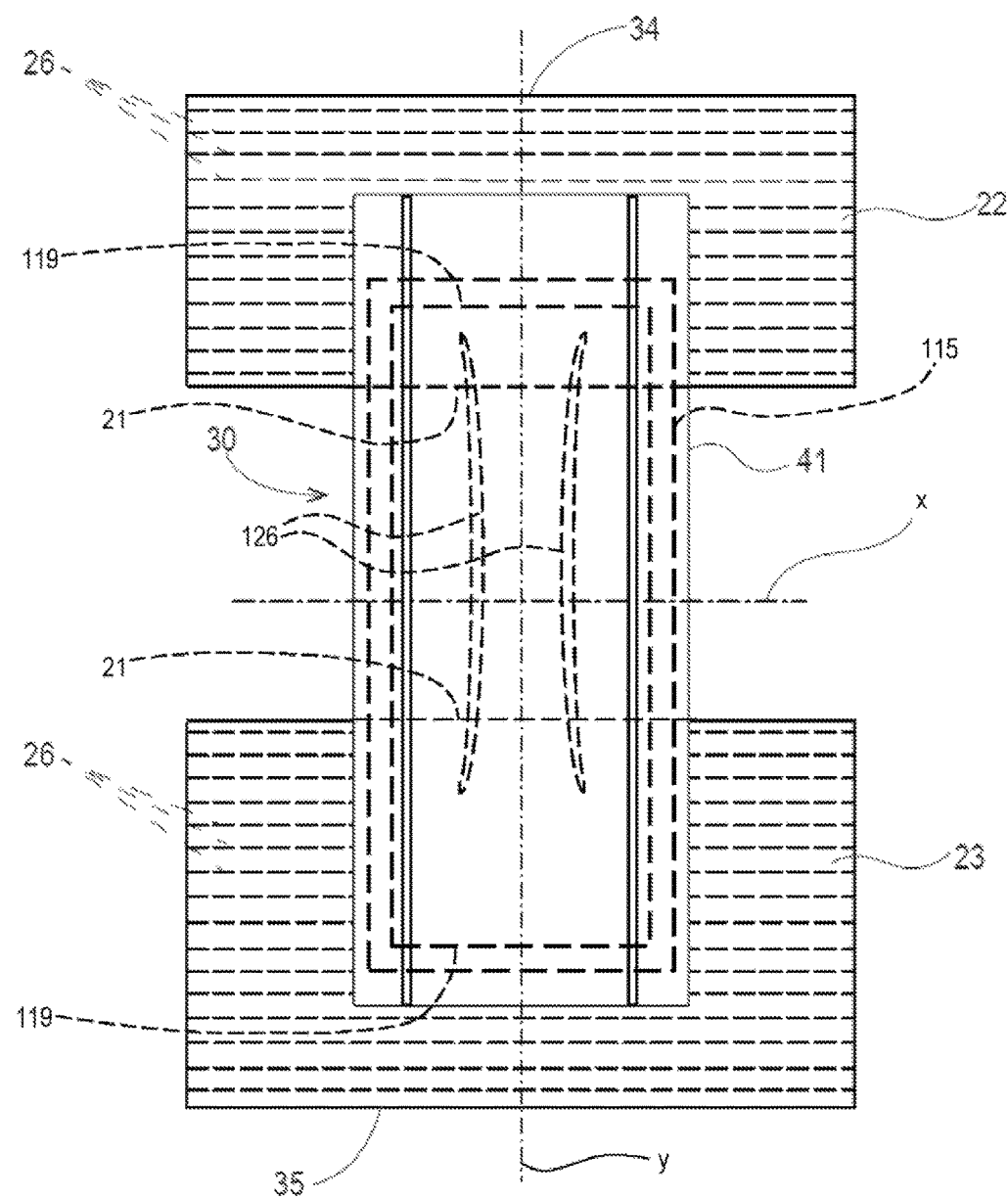
FIG. 16C is a schematic plan view of an alternate balloon pant precursor structure, prior to joining of the front and rear belt portions at side seams, wearer-facing surfaces facing the viewer, shown with another configuration of longitudinal main channels.
Figure 16D:
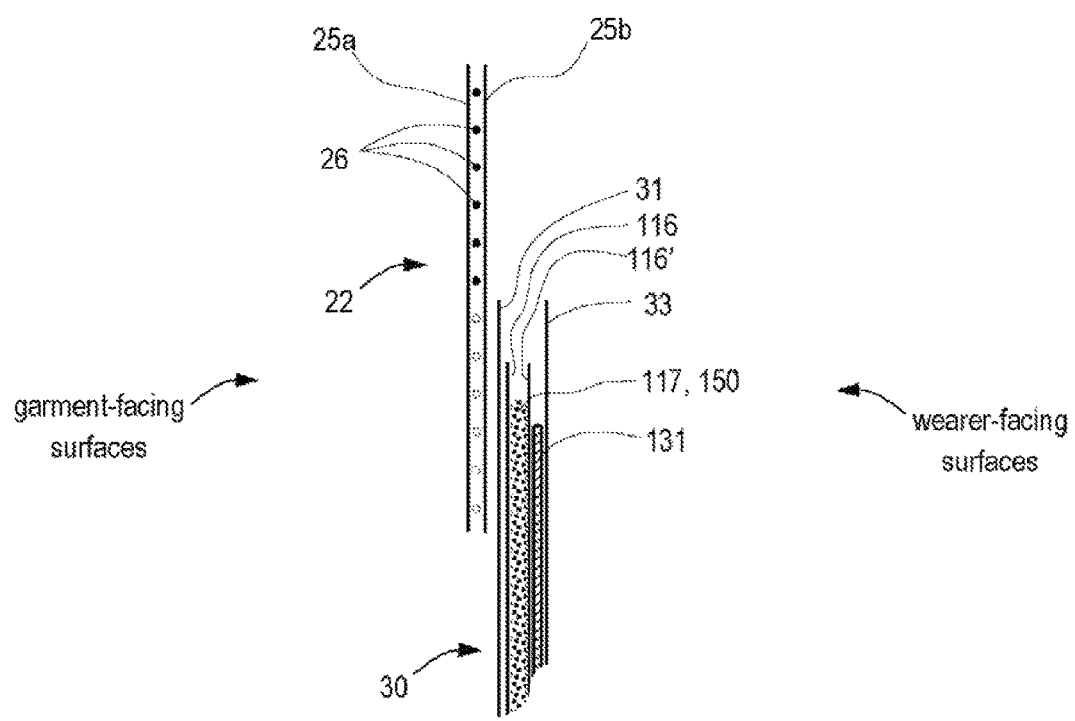
FIG. 16D is a schematic, exploded longitudinal cross section view of a portion of the structure depicted in FIG. 16A.

In another alternative, which may if desired be combined with any combination of the channel features described above, the absorbent layer 117 may extend longitudinally such that one or both ends 119 thereof are disposed beneath one or all layers of belt portions 22, 23 when the pant is worn. Non-limiting examples are suggested in FIGS. 16A-19. In a particular aspect, all longitudinally-oriented main channels 126 may extend such that one (FIGS. 16A, 16B) or both (FIG. 16C) ends thereof are disposed to the wearer side of one or both belt portions 22, 23 when the pant is worn. Non-limiting examples are suggested in FIGS. 16A-16D and 19. As a result, the ends of longitudinal chambers or other structures containing or defining deposits of absorbent polymer particles will, accordingly, be disposed to the wearer side of one or both belt portions when the pant is worn. In such a configuration, when the longitudinal chambers or other structures containing or defining deposits of absorbent polymer particles become longitudinally stiff from internal pressure as a result of liquid absorption, one or both ends thereof will be subject to lateral tensile forces in the belt portion(s). This may help restrain the end(s) of absorbent layer and hold them closer to the wearer's body, and thereby help prevent them from forming the bulges 219 such as are schematically illustrated in FIG. 7.

The absorbent layer, absorbent structure and/or configuration of channels may also have any features described in U.S. Pat. App. Pub. Nos. US2014/0163511; US2014/0163503; US2014/0163501; US2014/0163500; US2012/0316526; US2012/0316528; US2014/0163501; and US2014/0371701.

Absorbent Layer

The absorbent layer may include absorbent polymer particles 150 alone or in combination with other materials, such as cellulose fiber. The absorbent polymer particles may be immobilized on a substrate layer by, for example, a thermoplastic adhesive material 140.

Absorbent polymer particles suitable for use in the absorbent layer may include any absorbent polymer particles known from superabsorbent literature, for example such as described in Modern Superabsorbent Polymer Technology, F. L. Buchholz, A. T. Graham, Wiley 1998.

The absorbent polymer particles may be spherical, spherical-like, ellipsoid, or irregularly shaped, such as ovoid-shaped particles of the kind that may be obtained from inverse phase suspension polymerizations. The particles may, optionally, be agglomerated at least to some extent to form larger irregular agglomerations of particles.

The absorbent polymer particles may be selected from among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in the PCT Pat. App. Nos. WO 07/047598, WO 07/046052, WO2009/155265 and WO2009/155264.

In alternative examples, the absorbent layer may be substantially cellulose-free. Airfelt and other cellulose fiber have been used as absorbent fillers in absorbent cores of disposable diapers. Such fiber possesses absorbent properties and imparts some absorption capacity to an absorbent layer, but also may be included to provide a structural matrix to hold dispersed particles of absorbent polymer particles. While inclusion of such particles enhances absorption capacity, keeping such particles suitably dispersed may be important to prevent the particles from "gel-blocking" in use as they swell with absorbed liquid and block the passageways therebetween which allow liquid to move through deposits thereof, compromising absorption capacity. The inclusion of airfelt or other cellulose fiber as a matrix for absorbent polymer particles can serve to reduce or prevent gel-blocking. However, it also imparts bulk to an absorbent layer, even before absorption of any liquids. To reduce the overall size and/or thickness of the absorbent layer, and thereby improve wearer comfort and reduce the bulkiness of the pant for purposes of packaging and shipping volume efficiency, it may be desired to construct an absorbent core using the lowest volumes of core materials possible within performance constraints. Toward this end, examples of suitable materials and constructions for a suitable absorbent structure are described in, but are not limited to, U.S. patent application Ser. Nos. 12/141,122; 12/141,124; 12/141,126; 12/141,128; 12/141,130; 12/141,132; 12/141,134; 12/141,141; 12/141,143; and 12/141,146; and WO2008/155699. Generally, these applications describe absorbent layer constructions that minimize or eliminate the need for and inclusion of airfelt or other forms of cellulose fiber in combination with particles of absorbent polymer particles ("substantially cellulose-free" structures). Suitable methods for forming deposits of absorbent polymer particles are additionally disclosed in, for example, EP 1621167 A2, EP 1913914 A2 and EP 2238953 A2.

The absorbent polymer particles may be immobilized on the substrate layer. Immobilization may be achieved by applying a thermoplastic adhesive material, which holds and immobilizes the absorbent polymer particles, and cellulose when present, on the substrate layer. Some thermoplastic adhesive material may also penetrate into the layer of absorbent polymer particles and into the substrate layer to provide further immobilization and affixation. The thermoplastic adhesive material may not only help in immobilizing the absorbent polymer particles on the substrate layer but also may help in maintaining the integrity of the channels. The thermoplastic adhesive material avoids that a significant amount of absorbent polymer particles migrates into the channels.

Thermoplastic adhesive materials suitable for use in the present disclosure includes hot melt adhesives including at least a thermoplastic polymer in combination with a plasticizer and other thermoplastic diluents such as tackifying resins and additives such as antioxidants. Example suitable hot melt adhesive materials are described in EP 1447067 A2.

In some examples, the absorbent core may include an acquisition system, which is disposed between the topsheet and the wearer facing side of the absorbent structure. The acquisition system may serve as a temporary reservoir for liquid until the absorbent structure can absorb the liquid. The acquisition system may include a single layer or multiple layers, such as an upper acquisition layer facing towards the wearer's skin and a lower acquisition layer facing the garment of the wearer. The acquisition system may be in direct contact with the absorbent structure. In these examples, the acquisition system may fill in the channels or portions thereof of the absorbent structure. In some examples, the acquisition system, or one layer thereof, may be bonded to the substrate layer which undulates into the channels thus providing an undulating profile to said acquisition system.

As suggested in FIG. 15, the absorbent layer of the absorbent structure may include an acquisition/distribution layer 131. Layer 131 may have the form of, e.g., a layer, mat or other body formed of or including, e.g., comminuted cellulose fibers, or other hydrophilic natural, semi-synthetic or synthetic fibers or other material that may be used to form a mat, layer or other body.

In one example, one or both of the upper and lower acquisition layers may include a non-woven, which may be hydrophilic. Further, according to a certain example, one or both of the upper and lower acquisition layers may include the chemically cross-linked cellulosic fibers, which may or may not form part of a nonwoven material. According to an example, the upper acquisition layer may include a nonwoven, without the cross-linked cellulosic fibers, and the lower acquisition layer may include the chemically cross-linked cellulosic fibers. Further, according to an example, the lower acquisition layer may include the chemically cross-linked cellulosic fibers mixed with other fibers such as natural or synthetic polymeric fibers. According to example examples, such other natural or synthetic polymeric fibers may include high surface area fibers, thermoplastic binding fibers, polyethylene fibers, polypropylene fibers, PET fibers, rayon fibers, lyocell fibers, *eucalyptus* fibers and mixtures thereof. Suitable non-woven materials for the upper and lower acquisition layers include, but are not limited to SMS material, including a spunbonded, a melt-blown and a further spunbonded layer. In certain examples, permanently hydrophilic nonwovens, and in particular, nonwovens with durably hydrophilic coatings are desirable. Another suitable example includes an SMMS-structure. In certain examples, the nonwovens are porous.

Other Belt/Chassis Features

Figure 20:
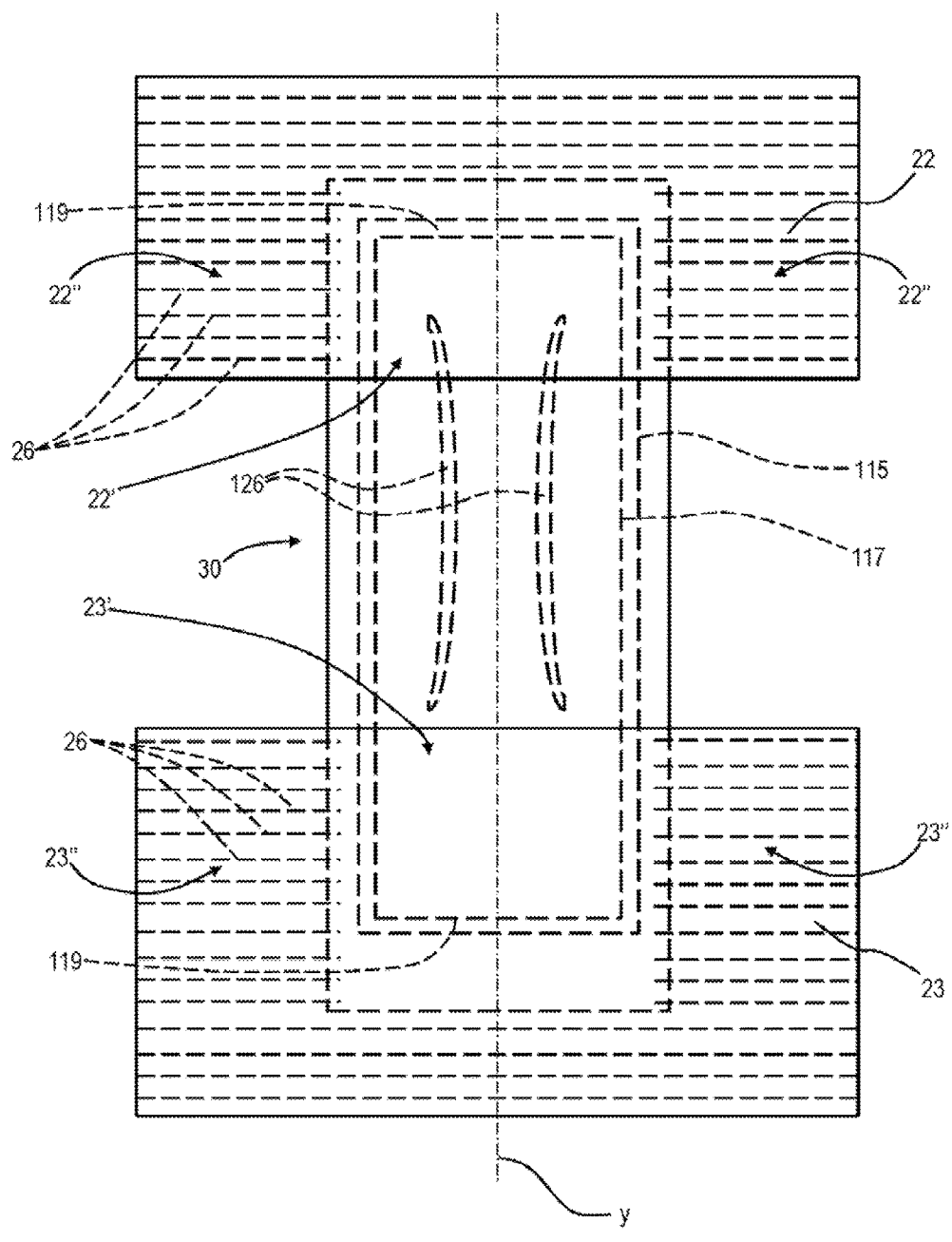
FIG. 20 is a schematic plan view of a balloon pant precursor structure, prior to joining of the front and rear belt portions at side seams, garment-facing surfaces facing the viewer, shown with a configuration of longitudinal main channels and non-elasticized zones in front and rear belt portions.

Referring to FIG. 20, elastic members such as elastic strands 26 may be configured within the front and/or rear belt portion(s) 22, 23 such that they are present in lower side zones 22", 23" of the belt portions, but not present in part of all of lower laterally central zones 22', 23' that overlie the chassis 30. Thus, one or both belt portions may be configured such that one or more of the layers that sandwich the elastic strands 26 are present in lower central zones 22', 23' of the belt portions, such as nonwoven layers 25*a*, 25*b* (see FIG. 3), without elastic stretch enabled by the presence pre-strained elastic members and ruffles of laterally gathered material. In the central zones 22', 23' that overlie the chassis, the nonwoven layer(s) of one or both belt portions 22, 23 may be disposed and affixed to the chassis material(s) (such as the backsheet) such that they overlie the chassis in laterally extended condition, i.e., they do not have longitudinal ruffles or rugosities (e.g., ruffles or rugosities 27, illustrated in FIGS. 4 and 5) that would otherwise be imparted by lateral contraction of pre-strained, sandwiched lateral elastic strands. In this configuration, the fully extended belt layer material(s) overlying the chassis 30 in lower central zones 22', 23', being without longitudinal ruffles and thereby being unable or less able to elastically stretch laterally as compared to the other elasticized, ruffled zones of the belt portions, are configured to provide greater resistance to lateral expansion, supplementing that of the chassis materials and helping to support and restrain the ends of absorbent layer 117. As a result, protrusion of outward bulges 219 upon absorption of liquid by the absorbent layer 117 (such as those illustrated in FIG. 7), may be reduced. This feature may be combined with any of the channel configurations described above, for potentially synergistic effects in reducing protrusion of bulges of the absorbent layer 117 as described above. Thus, in one example illustrated in FIG. 20, the forward ends of main longitudinal channels 126 may be disposed beneath (to the wearer-facing side) of non-elasticized lower central zone 22' of front belt portion 22. In some examples, the belt portions and the chassis may be configured to have features described in PCT/CN2014/094890, which describes additional examples of belt configurations having non-elasticized portions overlying the chassis.

In a further example, one or more elastic strands 26 present in the lower side zones 22", 23" may be selected (e.g., by decitex and/or tensile modulus) and/or configured (e.g., by longitudinal numerical count/unit longitudinal dimension of the belt, and/or amount of imparted pre-strain) to impart greater tensile contractive force to the belt structure in one or more of the lower side zones 22", 23" than in the upper zone(s) closer to the waist edges. This latter example may help enhance comfort of the pant, when worn, by providing for relatively lesser lateral contractive tensile force about the waist band areas and waist edges, and relatively greater lateral contractive tensile force with greater support, resistance to bulging of the channeled absorbent layer, and anchoring of the pant about the wearer's lower hips. Thus, one or more of the elastic strands 26 in one or both of lower side zones 22", 23" may have one or more of greater decitex, greater tensile modulus, greater number of strands 26 per unit longitudinal length of the belt portion, or greater amount of pre-strain, than one or more of the elastic strands 26 in the upper zone(s) closer to the waist edges in the same front or rear belt portion. This feature may be incorporated alone, or in combination with, the inclusion of non-elasticized central zone(s) 22', 23' of the belt described immediately above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A disposable absorbent pant, having a longitudinal axis, a lateral axis, a front region with a front waist edge, a rear region with a rear waist edge and a crotch region between the front and rear regions, comprising:
    an absorbent structure comprising an absorbent layer with at least one longitudinally-oriented elongate main channel formed therein, the main channel having a first length and respective frontward and rearward distal ends; and
    front and rear elasticized belt structure in each of the front and rear regions, each belt structure having an inner layer, an outer layer and a plurality of laterally-oriented strands of elastomeric material including a lowest strand disposed between the inner layer and the outer layer, a waist edge, and a lower edge formed by one or both of the inner and outer layers, the lower edge being disposed between the waist edge and the lateral axis,
    wherein the at least one main channel extends from the crotch region into at least one of the front region and the rear region such that at least one of the respective frontward and rearward distal ends of the main channel is disposed above the lowest strand of the front or rear elasticized belt structure.

2. The pant of claim 1 having at least one elongate secondary channel formed in the absorbent layer, the secondary channel having a second length, the second length being shorter than the first length and having a transverse direction component.

3. The pant of claim 2 wherein the secondary channel is disposed above the lower edge of one of the belt structures.

4. The pant of claim 2 wherein the secondary channel is disposed below the lower edge of one of the belt structures.

5. The pant of claim 2 wherein the secondary channel is curved or arcuate and is disposed in the front region.

6. The pant of claim 5 wherein the secondary channel has a curvature that is concave with respect to the front waist edge.

7. The pant of claim 2 in which the at least one secondary channel joins with the at least one main channel.

8. The pant of claim 1 having at least one elongate secondary channel formed in the absorbent layer in each of the front and rear regions, the at least one secondary channel in each region having a second length, the second length being shorter than the first length and having a transverse direction component.

9. The pant of claim 8 in which the secondary channel in each of the front and rear regions is curved or arcuate.

10. The pant of claim 9 wherein the secondary channel in the front region has a curvature that is concave with respect to the front waist edge, and the secondary channel in the rear region has a curvature that is convex with respect to the rear waist edge.

11. The pant of claim 1 wherein the at least one main channel extends from a point in the front region above the lowest strand of the front belt structure, through the crotch region and into the rear region to a point above the lowest strand of the rear belt structure.

12. The pant of claim 1 wherein each of the front and rear belt structures comprises a left zone disposed to the left of a left longitudinal edge of the absorbent structure, a right zone disposed to the right of a right longitudinal edge of the absorbent structure, and a center zone disposed between the left and right zones; and the at least one of the frontward and rearward distal ends of the main channel underlies the center zone of at least one of the front and rear belt structures to a wearer-facing side thereof.

13. The pant of claim 12 wherein the center zone overlying the frontward or rearward distal end of the main channel exhibits less lateral elastic stretch and contraction than the left and right zones.

14. The pant of claim 1 wherein the absorbent layer has at least two longitudinally-oriented elongate main channels formed therein, the main channels having a first length and respective frontward and rearward distal ends.

15. The pant of claim 14 wherein the at least two main channels are curved or arcuate.

16. The pant of claim 1 having left and right side seams at which the elasticized belt structure is affixed to an opposing belt structure, the left and right side seams each having a waist end and a leg opening end; and wherein the at least one of the frontward and rearward distal ends of the at least one main channel is disposed longitudinally above the leg opening end of each seam.

17. The pant of claim 16 wherein at least one of the left and right side seams is refastenable.

* * * * *